US006967016B2

(12) United States Patent
van Gemen et al.

(10) Patent No.: US 6,967,016 B2
(45) Date of Patent: Nov. 22, 2005

(54) METHOD OF DETERMINING THERAPEUTIC ACTIVITY AND/OR POSSIBLE SIDE-EFFECTS OF A MEDICAMENT

(75) Inventors: Bob van Gemen, Almere (NL); Eveline Catherina A. C. Timmermans, 's-Hertogenbosch (NL); Anthonij de Ronde, Amsterdam (NL); Irene Johanna M. Dobbelaer, Rosmalen (NL)

(73) Assignee: PrimaGen Holding B.V., Amsterdam (NL)

( * ) Notice: Subject to any disclaimer, the term of this patent is extended or adjusted under 35 U.S.C. 154(b) by 191 days.

(21) Appl. No.: 10/006,009

(22) Filed: Dec. 4, 2001

(65) Prior Publication Data

US 2002/0164612 A1 Nov. 7, 2002

(30) Foreign Application Priority Data

Dec. 4, 2000 (EP) .............................. 00204322
Jun. 6, 2001 (EP) .............................. 01202168

(51) Int. Cl.[7] .......................... A61K 49/00; C12Q 1/68; C12P 19/34
(52) U.S. Cl. .......................... 424/9.2; 435/6; 435/91.2; 435/91.51
(58) Field of Search .............................. 424/9.2; 435/6, 435/91.2, 91.51

(56) References Cited

U.S. PATENT DOCUMENTS 5,569,754 A * 10/1996 Williams et al.
6,221,600 B1 * 4/2001 MacLeod et al.
6,232,065 B1 * 5/2001 Robinson et al.
2002/0048763 A1 * 4/2002 Penn et al.
2002/0049176 A1 * 4/2002 Anderson et al.
2002/0169562 A1 * 11/2002 Stephanopoulos et al.
2003/0003488 A1 * 1/2003 Ramakrishnan
2003/0099933 A1 * 5/2003 Cote et al.

FOREIGN PATENT DOCUMENTS

| WO | WO 96/06191 A2 | 2/1996 |
| WO | WO 97/39149 A1 | 10/1997 |
| WO | WO 98/17826 A1 | 4/1998 |
| WO | WO 99/66075 A2 | 12/1999 |

OTHER PUBLICATIONS de Muys, J.–M. et al. Anti–human immunodeficiency virus type 1 activity, intracellular metabolism, and pharmacokinetic evaluation of 2'–deoxy–3'–oxa–4'–thiocytidine. Antimicrobial Agents and Chemotherapy 43(8):1835–1844 (Aug. 1999).*

Brinkman, K. et al. Mitochondrial toxicity of nucleoside analogue reverse transcriptase inhibitors: a looming obstacle for long–term antiretroviral therapy? Current Opinion in Infectious Diseases 13(1):5–11 (Feb. 2000).*

(Continued)

Primary Examiner—Diana B. Johannsen
(74) Attorney, Agent, or Firm—TraskBritt

(57) ABSTRACT

The invention relates to the diagnosis of disease or the determination of functioning of cellular organisms, being of multi-cellular or unicellular nature, being visible by the naked eye or being a microorganism. The invention provides a method for determining functioning of a cellular organism comprising determining the relative ratio of a first endosymbiont cellular organelle nucleic acid and/or gene product thereof in a sample obtained from the organism in relation to the amount of a second nucleic acid and/or gene product thereof.

15 Claims, 22 Drawing Sheets

Significant decrease of mtDNA in PBMC

OTHER PUBLICATIONS

Moyle, G. Clinical manifestations and management of anti-retroviral nucleoside analog–related mitochondrial toxicity. Clinical Therapeutics 22(8):911–936 (Aug. 2000).*

Williams R.S., Mitochondrial Gene Expression in Mammalian Striated Muscle. Evidence That Variation in Gene Dosage is the Major Regulatory Event, J. Biol. Chem., 261(26) :12390–12394 (1986).*

Williams et al., Regulation of Nuclear and Mitochondrial Gene Expression by Contractile Activity in Skeletal Muscle, □□J. Biol. Chem., 261(1) : 376–380 (1986).*

Voehringer et al., Gene microarray identification of redox and mitochondrial elements that control resistance or sensitivity to apoptosis. PNAS 97(6):2680–5 (Mar. 2000).*

DeRisi et al., Exploring the metabolic and genetic control of gene expression on a genomic scale.Science. 278(5338) : 680–6 (Oct. 1997).*

DeRisi et al., Use of a cDNA microarrays to analyze gene expression patterns in human cancer. Nature Genetics 14(4) : 457–460 (Dec. 1996).*

Schena M., Genome analysis with gene expression microarrays. BioEssays 18(5) : 427–431 (1996).*

Schena et al., Parallel human genome analysis: microarray-based expression monitoring of1000 genes. PNAS 93 (20) : 10614–9 (Oct. 1996).*

Schena et al., Quantitative monitoring of gene expression patterns with a complementary DNA microarray. Science 270 (5235) : 467–70 (1995).*

Lockhart et al., Expression monitoring by hybridization to high–density oligonucleotide arrays. Nature Biotechnology 14 (13) : 1675–80 (Dec. 1996).*

Partial European Search Report, EP 00 20 4322, dated Oct. 31, 2001.

Abbott, A.G., et al., "Quantitative variation in components of the maize mitochondrial genome between tissues and between plants with different male–sterile cytoplasms," 4 Plant Molecular Biology 233–240 (1985).

Anderson, C.M., et al., "Mitochondrial Electron Transport Complexes are Decreased in Skeletal Muscle in Type II Diabetes Mellitus," Abstracts from the 59th Session, p. a259 (Jun. 1999).

Boultwood, J., et al., "Amplification of mitochondrial DNA in acute myeloid leukaemia," 95 British Journal of Haematology 426–431 (1996).

Lee, H.K., et al., "Decreased mitochondiral DNA content in peripheral blood precedes the development of non–insulin–dependent diabetes mellitus," 42 Diabetes Research and Clinical Practice 161–167 (1998).

Su, C., et al., "Selective reduction of creatine kinase subunit mRNAs in striated muscle of diabetic rats," 263 American Journal of Physiology e310–e316 (1992).

Tepper, C.G., "Resistance of Mitochondrial DNA to Degradation Characterizes the Apoptotic but Not the Necrotic Mode of Human Leukemia Cell Death," 52 Journal of Cellular Biochemistry 352–361 (1993).

Partial European Search Report, International Application No. EP 00 20 4322, dated Oct. 31, 2001 (3 pages).

* cited by examiner

SEQUENCE LISTING

<160> NUMBER OF SEQ ID NOS: 46

<210> SEQ ID NO 1
<211> LENGTH: 48
<212> TYPE: DNA
<213> ORGANISM: Artificial Sequence
<220> FEATURE:
<223> OTHER INFORMATION: mtD p1

<400> SEQUENCE: 1
aattctaata cgactcacta tagggagaag agccgttgag ttgtggta        48

<210> SEQ ID NO 2
<211> LENGTH: 25
<212> TYPE: DNA
<213> ORGANISM: Artificial Sequence
<220> FEATURE:
<223> OTHER INFORMATION: MtD p2

<400> SEQUENCE: 2
tctccatcta ttgatgaggg tctta                                          25

<210> SEQ ID NO 3
<211> LENGTH: 34
<212> TYPE: DNA
<213> ORGANISM: Artificial Sequence
<220> FEATURE:
<223> OTHER INFORMATION: MtD mb

<400> SEQUENCE: 3
gcatgcccct cctagcctta ctactaatgc atgc                                34

<210> SEQ ID NO 4
<211> LENGTH: 49
<212> TYPE: DNA
<213> ORGANISM: Artificial Sequence
<220> FEATURE:
<223> OTHER INFORMATION: Mtd p 1_2

<400> SEQUENCE: 4
aattgtaata cgactcacta tagggaagaa ccgggctctg ccatcttaa                49

<210> SEQ ID NO 5
<211> LENGTH: 20
<212> TYPE: DNA
<213> ORGANISM: Artificial Sequence
<220> FEATURE:
<223> OTHER INFORMATION: mtD p2_2

<400> SEQUENCE: 5
gtaatccagg tcggtttcta                                                20

<210> SEQ ID NO 6
<211> LENGTH: 32
<212> TYPE: DNA
<213> ORGANISM: Artificial Sequence
<220> FEATURE:
<223> OTHER INFORMATION: mtd mb_2

<400> SEQUENCE: 6 ggaccccccca cacccaccca agaacagggt cc                                 32

<210> SEQ ID NO 7
<211> LENGTH: 49
<212> TYPE: DNA
<213> ORGANISM: Artificial Sequence
<220> FEATURE:
<223> OTHER INFORMATION: SnrpD p1

<400> SEQUENCE: 7
aattctaata cgactcacta tagggagagg cccggcatgt ggtgcataa                49

<210> SEQ ID NO 8
<211> LENGTH: 23
<212> TYPE: DNA
<213> ORGANISM: Artificial Sequence
<220> FEATURE:
<223> OTHER INFORMATION: SnrpD p2

<400> SEQUENCE: 8
ttccttacat ctctcacccg cta                                            23

<210> SEQ ID NO 9
<211> LENGTH: 32
<212> TYPE: DNA
<213> ORGANISM: Artificial Sequence

```
<220> FEATURE:
<223> OTHER INFORMATION: SnrpD mb

<400> SEQUENCE: 9
gcatgctgta accacgcact ctcctcgcat gc                           32

<210> SEQ ID NO 10
<211> LENGTH: 20
<212> TYPE: DNA
<213> ORGANISM: Artificial Sequence
<220> FEATURE:
<223> OTHER INFORMATION: SnrpD2 p2

<400> SEQUENCE: 10
tgcgcctctt tctgggtgtt                                         20

<210> SEQ ID NO 11
<211> LENGTH: 47
<212> TYPE: DNA
<213> ORGANISM: Artificial Sequence
<220> FEATURE:
<223> OTHER INFORMATION: mtR p1

<400> SEQUENCE: 11
aattctaata cgactcacta tagggaggag aagatggtta ggtctac           47

<210> SEQ ID NO 12
<211> LENGTH: 24
<212> TYPE: DNA
<213> ORGANISM: Artificial Sequence
<220> FEATURE:
<223> OTHER INFORMATION: MtR p2

<400> SEQUENCE: 12
cgatatggcg ttcccccgca taaa                                    24

<210> SEQ ID NO 13
<211> LENGTH: 34
<212> TYPE: DNA
<213> ORGANISM: Artificial Sequence
<220> FEATURE:
<223> OTHER INFORMATION: MtR mb

<400> SEQUENCE: 13
gctccgaagc ttctgactct tacctccccg gagc                         34

<210> SEQ ID NO 14
<211> LENGTH: 47
<212> TYPE: DNA
<213> ORGANISM: Artificial Sequence
<220> FEATURE:
<223> OTHER INFORMATION: MtR p1_2

<400> SEQUENCE: 14
aattctaata cgactcacta tagggagagg agacacctgc taggtgt           47

<210> SEQ ID NO 15
<211> LENGTH: 50
<212> TYPE: DNA
<213> ORGANISM: Artificial Sequence
<220> FEATURE:
<223> OTHER INFORMATION: MtR p1_3

<400> SEQUENCE: 15
aattctaata cgactcacta tagggagaag ggtagactgt tcaacctctt        50
```

<210> SEQ ID NO 16
<211> LENGTH: 22
<212> TYPE: DNA
<213> ORGANISM: Artificial Sequence
<220> FEATURE:
<223> OTHER INFORMATION: MtR p2_2

<400> SEQUENCE: 16
ggtgcccccg atatggcgtt cc                                              22

<210> SEQ ID NO 17
<211> LENGTH: 22
<212> TYPE: DNA
<213> ORGANISM: Artificial Sequence
<220> FEATURE:
<223> OTHER INFORMATION: MtR p2_3

<400> SEQUENCE: 17
gtaataatct tcttcatagt aa                                              22

<210> SEQ ID NO 18
<211> LENGTH: 49
<212> TYPE: DNA
<213> ORGANISM: Artificial Sequence
<220> FEATURE:
<223> OTHER INFORMATION: SnrpR p1

<400> SEQUENCE: 18
aattctaata cgactcacta tagggagagg cccggcatgt ggtgcataa                 49

<210> SEQ ID NO 19
<211> LENGTH: 23
<212> TYPE: DNA
<213> ORGANISM: Artificial Sequence
<220> FEATURE:
<223> OTHER INFORMATION: SnrpR p2

<400> SEQUENCE: 19
cagtatgcca agaccgactc aga                                             23

<210> SEQ ID NO 20
<211> LENGTH: 34
<212> TYPE: DNA
<213> ORGANISM: Artificial Sequence
<220> FEATURE:
<223> OTHER INFORMATION: SnrpR mb

<400> SEQUENCE: 20
cgtacgagaa gaggaagccc aagagccacg tacg                                 34

<210> SEQ ID NO 21
<211> LENGTH: 50
<212> TYPE: DNA
<213> ORGANISM: Artificial Sequence
<220> FEATURE:
<223> OTHER INFORMATION: Snrnpr p1_2

<400> SEQUENCE: 21
aattctaata cgactcacta tagggagaag aagatgacaa aggcctggcc                50

<210> SEQ ID NO 22
<211> LENGTH: 50
<212> TYPE: DNA
<213> ORGANISM: Artificial Sequence
<220> FEATURE:
<223> OTHER INFORMATION: SnrnpR p1_3

```
<400> SEQUENCE: 22
aattctaata cgactcacta tagggagaaa aaggcctggc ccctcatctt          50

<210> SEQ ID NO 23
<211> LENGTH: 19
<212> TYPE: DNA
<213> ORGANISM: Artificial Sequence
<220> FEATURE:
<223> OTHER INFORMATION: SnrnpR p2_2

<400> SEQUENCE: 23
tccatggcag ttcccgaga                                           19

<210> SEQ ID NO 24
<211> LENGTH: 20
<212> TYPE: DNA
<213> ORGANISM: Artificial Sequence
<220> FEATURE:
<223> OTHER INFORMATION: SnrnpR p2_3

<400> SEQUENCE: 24
cactatttat atcaacaacc                                          20

<210> SEQ ID NO 25
<211> LENGTH: 19
<212> TYPE: DNA
<213> ORGANISM: Artificial Sequence
<220> FEATURE:
<223> OTHER INFORMATION: SnrnpR p2_4

<400> SEQUENCE: 25
tcaatgagaa gatcaagaa                                           19

<210> SEQ ID NO 26
<211> LENGTH: 32
<212> TYPE: DNA
<213> ORGANISM: Artificial Sequence
<220> FEATURE:
<223> OTHER INFORMATION: SnrnpR mb_2

<400> SEQUENCE: 26
cgatcgagtc cctgtacgcc atcttccgat cg                            32

<210> SEQ ID NO 27
<211> LENGTH: 49
<212> TYPE: DNA
<213> ORGANISM: Artificial Sequence
<220> FEATURE:
<223> OTHER INFORMATION: Rubisco-DNA p1

<400> SEQUENCE: 27
aattctaata cgactcacta tagggggata atttcattac cttcacgag           49

<210> SEQ ID NO 28
<211> LENGTH: 21
<212> TYPE: DNA
<213> ORGANISM: Artificial Sequence
<220> FEATURE:
<223> OTHER INFORMATION: Rubisco-DNA p2

<400> SEQUENCE: 28
ggagtcctga actagccgca g                                        21

<210> SEQ ID NO 29
```

```
<211> LENGTH: 34
<212> TYPE: DNA
<213> ORGANISM: Artificial Sequence
<220> FEATURE:
<223> OTHER INFORMATION: Rubisco-DNA MB

<400> SEQUENCE: 29
gcatgcggta gataaactag atagctaggc atgc                            34

<210> SEQ ID NO 30
<211> LENGTH: 46
<212> TYPE: DNA
<213> ORGANISM: Artificial Sequence
<220> FEATURE:
<223> OTHER INFORMATION: Rubisco-RNA p1

<400> SEQUENCE: 30
aattctaata cgactcacta tagggagtt gttgttattg taagtc                 46

<210> SEQ ID NO 31
<211> LENGTH: 23
<212> TYPE: DNA
<213> ORGANISM: Artificial Sequence
<220> FEATURE:
<223> OTHER INFORMATION: Rubisco-RNA p2

<400> SEQUENCE: 31
caagtcctta tgaattccta tag                                        23

<210> SEQ ID NO 32
<211> LENGTH: 32
<212> TYPE: DNA
<213> ORGANISM: Artificial Sequence
<220> FEATURE:
<223> OTHER INFORMATION: Rubisco-RNA-MB

<400> SEQUENCE: 32
gctagcacac agggtgtacc cattatgcta gc                              32

<210> SEQ ID NO 33
<211> LENGTH: 48
<212> TYPE: DNA
<213> ORGANISM: Artificial Sequence
<220> FEATURE:
<223> OTHER INFORMATION: OryzaDNA p1

<400> SEQUENCE: 33
aattctaata cgactcacta tagggggatc ttaattacat gccgttca              48

<210> SEQ ID NO 34
<211> LENGTH: 20
<212> TYPE: DNA
<213> ORGANISM: Artificial Sequence
<220> FEATURE:
<223> OTHER INFORMATION: OryzaDNA p2

<400> SEQUENCE: 34
aaaggtgccg gttctcacta                                            20

<210> SEQ ID NO 35
<211> LENGTH: 36
<212> TYPE: DNA
<213> ORGANISM: Artificial Sequence
<220> FEATURE:
<223> OTHER INFORMATION: OryzaDNA mb

<400> SEQUENCE: 35
```

-continued

```
gctagcctct gcaagcttca tcagtaatag gctagc                                36

<210> SEQ ID NO 36
<211> LENGTH: 51
<212> TYPE: DNA
<213> ORGANISM: Artificial Sequence
<220> FEATURE:
<223> OTHER INFORMATION: OryzaRNA p1

<400> SEQUENCE: 36
aattctaata cgactcacta tagggctaa tgcccttttc ttttcttcct c                 51

<210> SEQ ID NO 37
<211> LENGTH: 20
<212> TYPE: DNA
<213> ORGANISM: Artificial Sequence
<220> FEATURE:
<223> OTHER INFORMATION: oryzaRNA p2

<400> SEQUENCE: 37
catattggct ttcgaagatt                                                  20

<210> SEQ ID NO 38
<211> LENGTH: 36
<212> TYPE: DNA
<213> ORGANISM: Artificial Sequence
<220> FEATURE:
<223> OTHER INFORMATION: OryzaRNA mb

<400> SEQUENCE: 38
gctagccttc agccattatt caagatggtg gctagc                                36

<210> SEQ ID NO 39
<211> LENGTH: 49
<212> TYPE: DNA
<213> ORGANISM: Artificial Sequence
<220> FEATURE:
<223> OTHER INFORMATION: tRNA-D-L p1

<400> SEQUENCE: 39
aattctaata cgactcacta tagggggtt ctagttcgag aaccgcttg                   49

<210> SEQ ID NO 40
<211> LENGTH: 21
<212> TYPE: DNA
<213> ORGANISM: Artificial Sequence
<220> FEATURE:
<223> OTHER INFORMATION: tRNA-L-D p2

<400> SEQUENCE: 40
gcgaaatcgg tagacgctac g                                                21

<210> SEQ ID NO 41
<211> LENGTH: 32
<212> TYPE: DNA
<213> ORGANISM: Artificial Sequence
<220> FEATURE:
<223> OTHER INFORMATION: tRNA-L-D mb

<400> SEQUENCE: 41
gctagccaac ttccaaattc agagaagcta gc                                    32

<210> SEQ ID NO 42
<211> LENGTH: 48
<212> TYPE: DNA
```

```
<213> ORGANISM: Artificial Sequence
<220> FEATURE:
<223> OTHER INFORMATION: petB RNA p1

<400> SEQUENCE: 42
aattctaata cgactcacta tagggaaacc ggtagcaact tgtactag       48

<210> SEQ ID NO 43
<211> LENGTH: 25
<212> TYPE: DNA
<213> ORGANISM: Artificial Sequence
<220> FEATURE:
<223> OTHER INFORMATION: petB RNA p2

<400> SEQUENCE: 43
ggtttcggta tctctggaat atgag                                25

<210> SEQ ID NO 44
<211> LENGTH: 33
<212> TYPE: DNA
<213> ORGANISM: Artificial Sequence
<220> FEATURE:
<223> OTHER INFORMATION: petB RNA MB

<400> SEQUENCE: 44
gctagcgagg gaacgtcttg agattcagct agc                       33

<210> SEQ ID NO 45
<211> LENGTH: 34
<212> TYPE: DNA
<213> ORGANISM: Artificial Sequence
<220> FEATURE:
<223> OTHER INFORMATION: SnrnpD mb_2

<400> SEQUENCE: 45
cgcatgctgt aaccacgcac tctcctcgca tgcg                      34

<210> SEQ ID NO 46
<211> LENGTH: 34
<212> TYPE: DNA
<213> ORGANISM: Artificial Sequence
<220> FEATURE:
<223> OTHER INFORMATION: MtD mb_3

<400> SEQUENCE: 46
cgtacgtgat atcatctcaa cttagtatcg tacg                      34
```

METHOD OF DETERMINING THERAPEUTIC ACTIVITY AND/OR POSSIBLE SIDE-EFFECTS OF A MEDICAMENT

CROSS-REFERENCE TO RELATED APPLICATIONS

This application claims priority under 35 U.S.C. 119(a)-(d) to European Patent Application 00204322.2, filed Dec. 4, 2000 and European Patent Application 01202168.9 filed Jun. 6, 2001, the contents of both of which are incorporated herein by this reference.

TECHNICAL FIELD

The invention relates to diagnosis of disease and/or determination of functioning of cellular organisms, of multicellular or unicellular nature, including organisms visible to the naked eye and microorganisms.

BACKGROUND

A diagnostician of disease studying (mal)functioning of cellular organisms can employ a broad range of inroads into the organism to obtain relevant information as to the various aspects of the malfunctioning. These inroads vary widely, examples of which include detecting relative ratios of kidney stones by studying urinary samples obtained from various patients, probing for the presence or absence of intestinal ulcers via endoscopy, scanning for detectable tumors by nuclear magnetic resonance ("NMR"), detecting diabetes by testing for insulin levels and/or glucose concentration in blood plasma, determining cancer proneness by determining transcriptional levels of oncogenes, and so on.

Currently, the detection of disease or malfunctioning (or vice versa, of health and proper functioning) of higher organisms, such as animals and plants, relies on testing samples obtained from these organisms and studying these samples in a laboratory. Often, when a fruitful method capable of determining, identifying or detecting (aspects of) a disease or malfunctioning of an organism has been found, it is also generally useful in testing or screening of compounds or methods for treatment of (aspects of) the disease or malfunctioning or useful in testing or screening for compounds or methods involved in causing (aspects of) the disease or malfunctioning. By using the same or similar methods used in diagnosis, it is generally possible to assess the usefulness of such candidate compounds or methods in treating and/or causing the disease or malfunctioning in question. Clearly, life science laboratories are always in the need of other inroads into organisms to obtain yet more information relating to disease or malfunctioning and to compounds and methods related to causing and/or treating the disease or malfunctioning.

DISCLOSURE OF THE INVENTION

The invention provides a method for determining (mal)functioning of a cellular organism comprising determining the relative ratio of an endosymbiont cellular organelle nucleic acid and/or gene product thereof in relation to another nucleic acid or gene product present in a sample obtained from the organism. In terms of the invention, "relative ratio" includes the amount of the first endosymbiont cellular organelle nucleic acid and/or gene product thereof in relation to the amount of the second nucleic acid and/or gene product thereof. The relative ratio may, for instance, be determined by (among other things) dividing the amount of the first nucleic acid or gene product thereof by the amount of the second nucleic acid or gene product thereof, or vice versa. The amount of one or both compounds may also be divided by, or subtracted from, a reference value. By determining functioning of a cellular organism is meant herein determining whether the cellular organism is in its natural healthy state, or whether the organism is somehow affected, for instance, by a disease and/or a (toxic) compound. The disease and/or (toxic) compound may affect the organism to such extent that clinical symptoms are present. Alternatively, the disease or (toxic) compound may have an influence upon the organism while clinical symptoms are not (yet) manifested.

Endosymbiont cellular organelles include those organelles of a eukaryotic cell that are thought to have been derived of prokaryotic bacteria very early on in the evolution of eukaryotic cells. These bacteria (as it is thought) have engaged in a symbiosis with early eukaryotic cells, and, at present, eukaryotic cells comprising these endosymbiont organelles in general cannot live without them. None of the present eukaryotic cells would function properly without mitochondria, and most plant cells would at least be considered to be malfunctioning when no proplastids, or organelles derived thereof, such as chloroplasts, etioplasts, amyloplasts, elaioplasts or chromoplasts were present. These organelles in general appear to be at least partially self-replicating bodies which, although under some nuclear controls, still possess considerable autonomy.

In particular, the invention provides a method whereby the relative ratio of an endosymbiont cellular organelle nucleic acid and/or gene product thereof is determined in relation to the amount of essentially nuclear nucleic acid detectable in the sample (be it DNA or RNA), or in relation to gene products (derivable by transcription and/or translation, such as mRNA or (poly)peptides) of the nuclear nucleic acid, (nuclear nucleic acid herein comprises chromosomal DNA and the RNA transcribed therefrom) for example, preset in nuclear or cytoplasmatic fractions or parts of the sample. DNA or corresponding mRNA encoding components of small nuclear ribonucleoprotein (SNRNP), or other essentially common nucleic acid derived from chromosomal DNA, is particularly useful to test, because of its ubiquitous presence. In this way, the invention provides a method for studying, for example, endosymbiont cellular organelle-related disease like mitochondrial and/or proplastid-related disease. By endosymbiont cellular organelle-related disease is meant herein a condition wherein the amount and/or at least one property of nucleic acid of the endosymbiont cellular organelle, and/or gene product thereof, is altered as compared to the natural situation. For instance, expression of the nucleic acid may be reduced. Endosymbiont cellular organelle-related disease, e.g., encoded by defects in the organelle's DNA, manifests in many different syndromes and is often variable in its expression (and thus in general hard to detect by testing for clinical parameters alone) due to heteroplasmy, whereby mutant and wild-type nucleic acid can be found in one cell, whereby its distribution can vary. Endosymbiont cellular organelle-related disease is often aggravated with increasing age of the affected individual. Endosymbiont cellular organelle-related disease can also often be observed after treatment against other disease with various drugs, and then contributes to various side-effects of those drugs that one would like to avoid during treatment. Those side-effects can now be better studied by using a method as provided herein.

Furthermore, the invention provides a method whereby the relative ratio of a first endosymbiont cellular organelle nucleic acid and/or gene product thereof is determined in relation to the amount of a second (distinct) endosymbiont cellular organelle nucleic acid detectable in the sample (be it DNA or RNA), or in relation to gene products (derivable by transcription and/or translation, such as mRNA or (poly) peptides)) of the endosymbiont cellular organelle nucleic acid. In one aspect of the invention, the method involves determining a ratio between organelle DNA, such as mtDNA, and the corresponding transcriptionally derivable organelle RNA, in the example the related mtRNA, or translated gene product. This way, the level of transcription and/or translation can be determined. An alteration of the level of transcription and/or translation, as compared to the natural level of transcription and/or translation, is indicative for an altered functioning of the organelle. The altered functioning may be malfunctioning of the organelle, because of a disease and/or because of side-effects of a certain treatment. The malfunctioning may, for instance, comprise a decreased level of transcription. Alternatively, the altered functioning may be an improved functioning of the organelle, for instance, during treatment and/or curing of an endosymbiont cellular organelle-related disease.

The malfunctioning may also comprise an increased level of transcription. A disease, or a treatment of a disease, may involve decrement of the amount of endosymbiont organelle DNA. However, the decrement can at least in part be compensated by an increase in transcription of the DNA, at least in the first stage of the disease. This way, the amount of RNA derived from the endosymbiont organelle DNA may not be decreased at all, or relatively less decreased as compared to the amount of the endosymbiont organelle DNA. Symptomatic side-effects of the disease or treatment may then not be (fully) sensed yet. However, upon further decrement of the amount of the endosymbiont organelle DNA, the amount of RNA derived from the DNA will eventually also drop significantly. Side-effects can then occur. Conventionally, upon manifestation of side-effects, a disease is treated or a treatment is reduced or stopped. However, in this conventional way, a patient already suffers from the side-effect(s). With a method of the invention, however, side-effect(s) involving clinical symptoms can be predicted. For instance, an altered level of transcription and/or translation of an endosymbiont cellular organelle nucleic acid is indicative for altered functioning of a cellular organism, for instance, malfunctioning of the organism involving (future) side-effects. An alteration of the relative ratio of endosymbiont cellular organelle DNA and/or gene product thereof in relation to the amount of nuclear nucleic acid or gene product thereof is also indicative of altered functioning of a cellular organism.

In yet another aspect of the invention, the ratio between two distinct organelle DNA's or related gene products is determined. In one aspect, a method of the invention is provided wherein the first endosymbiont cellular organelle nucleic acid and the second endosymbiont cellular organelle nucleic acid are obtained from the same kind of organelle. The organelle, for instance, comprises a mitochondrion.

A method of the invention is particularly suitable for staging of a disease. An organism can already be affected by a disease, while no or little clinical symptoms are essentially present yet. However, although no clinical symptoms are essentially present, the relative ratio of a first endosymbiont cellular organelle nucleic acid and/or gene product thereof in relation to the amount of a second nucleic acid and/or gene product thereof can already be altered. As shown in the examples, the alteration of the relative ratio can be determined before clinical symptoms and/or conventional tests, like determination of the lactate pyruvate ratio, to indicate an altered functioning of an organism. Thus, the relative ratio is very suitable for determining the stage of a certain disease. The invention therefore provides in one aspect a method for determining the staging of a disease, comprising determining the relative ratio of an endosymbiont cellular organelle nucleic acid and/or gene product thereof in a sample obtained from an organism suffering from or at risk of suffering from the disease.

A method of the invention for staging of a disease can be used for diagnosis. For instance, people can be routinely tested by a method of the invention with certain time intervals. Alternatively, people can be tested at the moment that they have some clinical symptoms. An alteration in the relative ratio is indicative of a certain degree of disease. The kind of the disease need not be diagnosed by a method of the invention.

Other possible uses of the invention lay in candidate drug testing for beneficial activity and/or side-effects of possible medicaments or pharmaceutical compositions such as candidate anti-parasitic compounds, antibiotic compounds, cytostatic compounds, and so on. For example, the invention provides a method for determining therapeutic activity and/or possible side-effects of a candidate compound, for example, in determining its usefulness for treatment of malfunctioning of a cellular organism, comprising determining the relative ratio of an endosymbiont cellular organelle nucleic acid and/or gene product thereof in a sample obtained from the organism, preferably the organism or an essentially related organism, such as belonging to the same species or genus, having been provided with the compound. If the relative ratio of an endosymbiont cellular organelle nucleic acid, and/or gene product thereof, of a certain organism is altered after the candidate compound is administered to the organism, this indicates therapeutic activity and/or side-effects involved with the compound when administered to the organism. Additionally, this also indicates therapeutic activity and/or side-effects involved with the compound in an essentially related organism. Therefore, for determining therapeutic activity and/or side-effects of a candidate compound for treatment of malfunctioning of a cellular organism, it is not necessary to use exactly the same organism in a method of the invention. An essentially related organism can also be used.

In another aspect, the invention provides a method for determining therapeutic activity and/or possible side-effects of a medicament comprising determining the relative ratio of an endosymbiont cellular organelle nucleic acid and/or gene product thereof in a sample obtained from an organism, preferably the organism having been provided with the medicament. In terms of the invention, therapeutic activity means the capability of at lest in part treating a disease. In one embodiment of the invention, the therapeutic activity comprises a therapeutic activity against an HIV-related disease and/or a tumor-related disease. The medicament may, for instance, comprise a cytostaticum, optionally combined with other antiretroviral therapy. According to the ATHENA-study in the Netherlands, forty percent of the patients undergoing an antiretroviral therapy need to change antiretroviral therapy because of adverse side effects. Therefore, a method of the invention is very much desired during such therapies, because the method can detect side-effects before (severe) clinical symptoms are essentially present. The therapy can then already be stopped and/or changed before the clinical effects are essentially present. In that case, the clinical symptoms may not, or to a lesser extent, become present. This will prevent a lot of suffering.

Thus, in a preferred aspect, a method of the invention is provided wherein the side-effects are not essentially manifested at the moment that the method is performed. In terms of the invention, by "not essentially manifested" is meant that the side-effect is not (yet), or only partly, manifested by clinical symptoms.

In one aspect, a method of the invention is provided wherein the compound or medicament comprises a cytostaticum. Commonly used cytostatica, for instance, comprise alkylating compounds, antimitotoxic cytostatica, antitumor antibiotica, and topo-isomerase inhibitors. Nonlimiting examples thereof comprise chloorambucil, cyclofosfamide, estramustine, ifosamide, melfalanthiotepabusulfan, treosulfancarmustne, lomustinecisplatine, carboplatine, oxaliplatinedacarbazine, procarbazine, temozolomide vinblastine, vincristine, vindesinedocetaxel, paclitaxeldaunorubicine, doxorubicine, epirubicine, idarubicine, mitoxanthronbleomycine, dactinomycine, mitomycineirinotecan, topotecanetoposide, teniposide amsacrine, asparaginase, cladribine, hydroxycarbamide, pentostatine methotrexate and/or raltitrexed. During antiretroviral treatment, and/or treatment of tumor-related disease, a nucleoside and/or nucleotide analogue is often used. These analogues involve a high risk of side-effects, because they interfere with replication and/or transcription processes in an organism. The amount of endosymbiont cellular organelle nucleic acid is then often altered as well. Therefore, a method of the invention is very suitable when an organism is treated with a medicament involving nucleoside and/or nucleotide analogues.

In one aspect, the invention provides a method of the invention wherein the compound or medicament comprises a nucleoside and/or nucleotide analogue. Nonlimiting examples of such analogues are fludarabine, mercaptopurine, thioguanine, cytarabine, fluorouracil, and/or gemcytabine. In yet another aspect, a method of the invention is provided wherein the compound or medicament comprises AZT, ddI, ddC, d4T, 3TC and/or tenofofir. In a method of the invention, the organism of an essentially related organism has preferably been provided with the compound or organism.

Treatment of certain diseases, like, for instance, an HIV-related disease, has to be performed during a long period of time. A method of the invention is particularly suitable during treatment of a disease during a long period of time. During the long period, many side-effects can evolve, and a patient can now be monitored regularly even though no clinical symptoms are present (yet). Therefore, in one aspect, a method of the invention is provided wherein the medicament is used during at least 3 months, preferably during at least 6 months, and more preferably during at least 12 months. In one aspect, the medicament is used for treatment of a chronic disease. By a chronic disease is meant herein a disease which cannot be completely cured. Once an individual has acquired the disease, the disease is always present in the individual, albeit the clinical symptoms may vary widely. The symptoms may sometimes even be unnoticed by the individual. A chronic disease, for instance, comprises an HIV-related disease.

By a side-effect of a compound is meant herein another effect than the purpose of the compound. The side-effect may be an unwanted effect. For instance, a therapeutic compound may counteract a disease and simultaneously reduce the metabolism of an organism. The reduction of the metabolism is then referred to as a (negative) side-effect. Alternatively, a side-effect of a compound may be a beneficial effect, like, for instance, immunity against yet another disease.

Also, use for (selective) toxin testing of, e.g., herbicides, insecticides, anti-parasitic compounds, and antibiotic compounds is provided herein. The invention provides a method for determining toxic activity of a candidate compound, for example, in determining its usefulness for causing malfunctioning of a cellular organism, e.g., by having a cytostatic or even cytotoxic effect, comprising determining the relative ratio of an endosymbiont cellular organelle nucleic acid and/or gene product thereof in a sample obtained from an organism, preferably the organism or related organism having been provided with the compound.

In a preferred embodiment, selectivity is also tested, using or applying the method as provided herein (preferably in parallel experiments) on or to a first organism and on or to an essentially related second organism, if desired, belonging to a different family or order, but preferably belonging to at least a different class or phylum, most preferably belonging to a different kingdom of organism. Selectivity aspects are, for example, tested by testing the compounds in (if desired only in cells of) a first target organism (such as a bacterium or parasite) as well as testing the host or cells thereof, being an essentially unrelated second organism, for example, a mammal or plant, or by testing of a crop plant or cells thereof as well as testing an essentially unrelated weed plant or cells thereof with the compound to determine, for example, selective toxic or selective therapeutic effects. It is also provided to test normal cells derived from an individual in parallel or comparison with aberrant cells, such as tumor cells derived from the same individual, to detect or screen for a tumor-specific or at least selective cytostatic or cytotoxic compound for use in therapy of the individual or others with similar or related disease.

With a method of the invention, a relative ratio is, for instance, determined by measuring the amount of the nucleic acid(s) and/or gene product(s) present in the sample, usually after at least one processing step, like, for instance, amplification of target nucleic acid. After the amounts have been measured, the relative ratio can be determined by dividing one amount by another.

Minute amounts of target nucleic acid can be detected and quantified by using enzymatic amplification. Examples of enzymatic amplification techniques are a polymerase chain reaction (PCR)[1], nucleic acid sequence-based amplification (NASBA)[2], SDA, TMA, and others. Specific amplification of a target nucleic acid sequence can be achieved by adding two primer sequences to a reaction. An amplified region can be detected at the end of an amplification reaction by probes that are specific for the amplified region. Alternatively, an amplified region can be detected during generation of the amplified nucleic acid in the amplification reaction[3]. In the latter protocol, a signal of a label attached to a probe can become detectable after the probe has hybridized to a complementary nucleic acid. Examples of such probes that enable real-time homogeneous detection in amplification reactions are TaqMan[3] and Molecular Beacon probes[4,5].

Quantification of a target nucleic acid sequence is commonly accomplished by adding a competitor molecule, which is amplified using the same primers and which contains sequences that allow discrimination between the competitor and target nucleic acid sequence[2,6]. The ratio between the amplified competitor and target nucleic acid sequence can be used to quantify the target nucleic acid sequence. Detection of the competitor or target nucleic acid sequence can, for instance, be achieved at the end of the amplification reaction by probes that are specific for the amplified region of competitor or target nucleic acid sequence or during generation of the amplified nucleic acid in the amplification reaction. In the latter protocol, a signal of a label attached to a probe can become detectable after the probe has hybridized to a complementary target nucleic acid and when the target has exceeded a threshold level, the time or cycle number to positivity. In other methods for quantification, the time to positivity can be used for quantification without addition of a competitor[7].

A method of the invention is very suitable for, among others, determining (mal)functioning of a cellular organism, candidate drug testing and selective toxin testing. Many reactions have been carried out using a method of the invention, which has proven to be a useful tool (see examples). An even more precise result can be obtained using a method of the invention when double spreading in the result is avoided. Generally, double spreading in the result of a method of the invention is obtained due to varieties in conditions in different reaction mixtures. For instance, to be able to detect and quantify specific nucleic acids present in a sample, an amplification step is often necessary. However, the temperature of the reaction mixture of nucleic acid 1 may be slightly higher than the temperature of the reaction mixture of nucleic acid 2. This may result in a higher yield of nucleic acid 1 and, hence, in a higher ratio of the amount of nucleic acid 1 versus nucleic acid 2 than would have been obtained if the temperature of reaction mixture 1 had been exactly the same as the temperature of reaction mixture 2. Because of the temperature difference in the reaction mixtures, the determined ratio is not exactly the same as the real ratio of the two nucleic acids present in the initial sample. Likewise, minute variations in other conditions like, for instance, the amount of enzyme added can lead to variations in the determined amounts of nucleic acids 1 and 2. Thus, the measured amounts of nucleic acids 1 and 2 may vary independently from each other. Independent variations in the determined amounts may result in an even larger variation in the calculated ratio of the measured amounts. This is called double spreading in the result. Thus, by double spreading is meant herein at least one variation in an obtained result, due to a variety of at least one reaction condition in at least two reaction mixtures. For instance, also the total amount of volume may differ slightly between two reaction mixtures.

In some particular cases, double spreading in a result may exceed the variations of the relative ratio of an endosymbiont cellular organelle nucleic acid and/or gene product thereof in an organism which is due to a certain disease or treatment. For instance, inhibitors of viral polymerase are often used for treatment of HIV. Inhibitors of viral polymerase may also affect mitochondrial polymerase gamma. Thus, the amount of mitochondrial polymerase gamma may be reduced during the treatment of HIV, which may result in a decreased amount of mitochondria per cell. A decrement of, for instance, 50% of the mitochondria may result in side-effects. The ratio of mitochondrial DNA versus nuclear DNA may be diminished by a factor of 2. However, a decrement of mitochondrial DNA by a factor of 2 can, in some cases, lie within the double spreading of the measurement of the ratio because of the mentioned variations in conditions. Therefore, this biologically important difference in the amount of mitochondria may not reliably be detected because of double spreading in the result. Thus, double spreading can, in some cases, reduce the reliability of detection of biologically important differences in a ratio of nucleic acids and/or their gene products. Therefore, one embodiment of the present invention provides a method for determining functioning of a cellular organism, without double spreading in the result, comprising determining the relative ratio of a first endosymbiont cellular organelle nucleic acid and/or gene product thereof in a sample obtained from the organism in relation to the amount of a second nucleic acid and/or gene product thereof. The double spreading can, in a preferred embodiment of the present invention, be prevented by determination of the ratio in the same assay. This means that a processing step and/or a measurement of the amounts of at least 2 nucleic acids and/or gene products thereof is performed in the same assay. In terms of the invention, an assay typically utilizes one reaction mixture. Preferably, all components of an assay of the invention are mixed randomly in the assay. The reaction mixture may be present in one reaction tube.

However, a person skilled in the art can think of more methods to prevent double spreading in the result. He/she can, for instance, use a reaction vessel which is divided into different parts by a (semi)permeable membrane. As long as at least one reaction condition varies dependently in the different parts, double spreading is avoided and the obtained result will be more accurate.

In one embodiment of the current invention, at least two target sequences are amplified in one assay. The two target sequences may be the endosymbiont cellular organelle nucleic acid and the second nucleic acid. Thus, in one embodiment of the current invention, a method of the invention is provided, comprising amplification of the endosymbiont cellular organelle nucleic acid and the second nucleic acid in the same assay. When at least two target sequences are amplified in one assay, varieties in reaction conditions in the assay can influence the obtained amount of each sequence present in the assay dependently. For instance, the obtained amount of each sequence present in the assay will be influenced by the same temperature, the same overall volume and so on. Detection of the two target sequences can be achieved by using two specific probes during the generation of an amplified nucleic acids during an amplification reaction. The two probes may each have a different label allowing discrimination between the two probes and thereby between the two different target sequences. Quantification can be achieved by relating the time to positivity as well as the slope of the relative fluorescence increase of both real time amplification reactions. Preferably, a reference curve is created before. The quantification of the nucleic acid can then be performed by comparing the obtained value(s) with the reference curve. Thus, there is no need for an internal standard like, for instance, a competitor molecule. A method of relative quantification of two targets in one assay has an improved accuracy compared to quantification in two separate assays and requires less handling time and reagents. We found that duplexing of two amplification reactions in the same tube gives an immediate indication of the ratio of the two targets. The conditions of both amplification reactions are the same, ruling out variations of those conditions without the necessity for internal or external calibrators. Hence, double spreading in the result is now avoided. Thus, in one aspect, the invention provides a method, wherein a relative ratio is determined directly by dividing one amount of nucleic acid by another. Preferably, the relative ratio is determined by comparison with a reference curve. In terms of the invention, "determined directly" means that an immediate indication of the ratio of the two targets is possible, for instance, by comparing the intensity of the two different fluorescent labels of the two specific probes. In this embodiment, dividing one amount of nucleic acid by another is performed by dividing the intensity of the corresponding flourescent label by another. No internal standards are used in a method of the invention wherein the relative ratio is determined directly.

In one aspect, a method of the invention is provided wherein the cellular organelle nucleic acid, the gene product thereof, the second nucleic acid and/or the gene product thereof is obtained from a peripheral blood mononuclear cell (PBMC) and/or a fibroblast. Especially the use of PBMCs is preferred because then a blood sample from the organism can be used. A blood sample is easy to obtain and relatively large amounts are often available. Therefore, in a preferred embodiment, a method of the invention is provided wherein the sample comprises a blood sample.

A method of the invention especially useful to quantify a target nucleic acid and/or gene thereof with a variable content in relation to a target nucleic acid and/or gene product thereof with a constant content. An example is the quantification of the variable cellular content of mitochondrial DNA to the constant cellular content of the DNA of a nuclear gene (two per diploid cell). Another example comprises the quantification of variably expressed RNA like mitochondrial RNA to constitutively expressed RNA that is essential for cell survival like the SNRP U11A encoding RNA involved in splicing or other essentially common nucleic acids derived from nuclear DNA with a ubiquitous presence. We found that it is possible to determine a relative ratio of a factor 2:3.

In one aspect, the invention provides a method of the invention wherein the first nucleic acid comprises RNA and the second nucleic acid comprises DNA. A method of the invention is, for instance, particularly suitable for the quantification of the cellular content of mitochondrial RNA to the cellular content of the DNA of a nuclear gene like U1A. This is shown in example 22.

Furthermore, the invention provides a diagnostic kit comprising at least one means for performing a method according to the invention, the kit comprising at least one primer or prove set selective for the amplification and detection of a nucleic acid related to or derived from endosymbiont cellular organelles and, when so desired, necessary amplification reagents, such as can be found exemplified in the detailed description herein or which are otherwise known in the art. In particular, the invention provides a diagnostic kit wherein the kit comprises more than one primer or probe set for the amplification of nucleic acid sequences related to cellular organelles, preferably supplemented with a primer or probe set for the amplification of nucleic acid related to the chromosomes, such as an SNRP specific primer or probe. In particular, the invention provides a kit comprising at least one primer or probe from table 1 for the amplification of nucleic acid sequences related to cellular organelles. It is, of course, preferred that the amplification reagents, when provided with the kit, comprise an enzyme with reverse transcriptase activity, such as required for PCR or NASBA amplification. Of course, a kit comprising a means for the detection of a gene product other than nucleic acid for use in a method according to the invention is herewith also provided.

The invention furthermore provides the use of a compound obtainable or detectable by a method according to the invention in the preparation of a medicament, a herbicide, insecticide, anti-parasiticum, cytostatic, etc., and a medicament, herbicide, insecticide, anti-parasiticum, etc. obtainable or derivable or identifiable by a method according to the invention.

The invention is further explained in the detailed description herein, wherein most examples are directed by way of example at testing of mitochondria, being central to the provision and use of energy in a cell; however, it will easily be understood that the same principles apply to tests using other endosymbiont organelles, such as chloroplasts, being central to the provision of carbohydrates to a plant cell.

EXAMPLES

Used ingredients and general methodology

In table 1, the primers and probes used in the examples are summarized. Standard NASBA nucleic acid amplification reactions were performed in a 20 $\mu$l reaction volume and contained: 40 mM Tris-pH 8.5, 70 mM KCl, 12 mM $MgCl_2$, 5 mM dithiothreitol, 1 mM dNTP's (each), 2 mM rNTP's (each), 0.2 $\mu$M primer (each), 0.05 $\mu$M molecular beacon, 375 mM sorbitol, 0.105 $\mu$g/$\mu$l bovine serumn albumin, 6.4 units AMV RT, 32 units T7 RNA polymerase, 0.08 units RNAse H and input nucleic acid. The complete mixture, except the enzymes, sorbitol and/or bovine serum albumin was, prior to adding the enzyme mixture, heated to 65° C. for 2 minutes in order to denature any secondary structure in the RNA and to allow the primers to anneal. After cooling the mixture to 41° C., the enzymes were added. The amplification took place at 41° C. for 90 min in a fluorimeter (CytoFluor 2000) and the fluorescent signal was measured every minute (using the filter set 530/25 nm and 485/30 nm). For amplification of DNA target sequences, the 65° C. denaturation step was replaced with a 95° C. denaturation step for 2 to 5 minutes.

To achieve quantification, a dilution series of target sequences for a particular primer set was amplified and the time points at which the reactions became positive (the time to positivity, TTP) were plotted against the input amounts of nucleic acid. This way a calibration curve was created that could be used to read TTP values of reactions with unknown amounts of input and deduce the input amount. Examples of typical standard curves for quantification of RNA and DNA are shown in FIG. 1.

For some of the target sequences, no dilution series were available with reliable absolute amount of copies determined. Those series were given an arbitrary unit as measurement instead of DNA or RNA copies, e.g., cell-equivalent or ET-unit. As a result, it sometimes seems that there is less RNA than DNA, which is quite the opposite of what is expected.

Cells (fibroblasts and PBMC's) were cultured under standard conditions in standard media known to persons skilled in the art with the addition of drugs or putative toxic or stimulating compounds as defined in the examples. Nucleic acids were isolated from the cells with the method described by Boom et al. (Boom, R.; Sol, C.J.; Salimans, M.M.; Jansen, C.L.; Wertheim-van Dillen, P.M.; van der Noordaa, J.; 1990. Rapid and simple method for purification of nucleic acids. *J Clin Microbiol*; 28(3):495–503) or with dedicated isolation kits purchased from Qiagen (Qiagen GmbH, Max Volmer Strasse 4, 40724 Hilden, Germany) and used according to the manufacturer's protocols. A small aliquot of the isolated nucleic acid was analyzed on an agarose gel and the remainder stored at –80° C. until further analysis. Usually the nucleic acid was diluted 10 times with water, and of the diluted nucleic acid, usually 5 $\mu$l was used as input in the NASBA amplification reactions.

Example 1

In this example it is explained what kind of ratio's can be measured with a method according to the invention and the meaning they can have in a diagostic sense:

The invention, for example, provides determining the relative ratio of organelle DNA to chromosomal DNA. This ratio, when compared with normal values or determined at at least two points in time, shows the decline or increase of organelles per cell. Also is provided determining the ratio of organelle RNA to chromosome-encoded RNA. This ratio, when compared with normal values or determined at at least two points in time, shows the organelle transcription activity decline or increase per cell, normalized for the active state (i.e., transcription state) of the cell.

Determining the ratio of organelle RNA to chromosomal DNA is also provided. This ratio, when compared with normal values or determined at at least two points in time, shows the organelle transcription activity decline or increase per cell.

Determining the ratio of organelle DNA to organelle RNA is also provided. This ratio, when compared with normal values or determined at at least two points in time, shows the decline or increase of transcription in the organelle, indicating regulation at the transcriptional level to achieve a certain mRNA (and therefore protein) level.

Determining the ratio of organelle DNA to chromosome encoded RNA is also provided. This ratio, when compared with normal values or determined at at least two points in time, shows the decline or increase of transcription in the cell, in relation to chromosomal RNA transcription levels, indicating the activity state of the organelle, which is especially useful when chromosomal RNA is determined that encodes an organelle protein or other component thereof.

Example 2

Fibroblast cells were cultured in vitro in the presence of the antiviral drugs ddC, AZT and D4T at two concentrations each, 3 μM and 30 μM, respectively, for 4 weeks. As controls, cell cultures with ethidium bromide and without drugs were also performed. Ethidium bromide is known to deplete mitochondrial DNA completely from cells and is a positive control in terms of achieving an effect on the mitochondria content of cells. At one week intervals, part of the cells was harvested and analyzed for an amount of mitochondrial DNA (primers MtD p1 and MtD p2 and probe MtD mb) and chromosomal DNA (primers SnrpD p1 and SnrpD p2 and probe SnrpD mb) in the described NASBA protocol. The cultures with AZT, D4T and without additive showed no measurable change in mitochondrial DNA to chromosomal DNA ratio in the culture period of 4 weeks. The culture with ethidium bromide showed a decline in mitochondrial DNA content as expected. The results for ddC are shown in FIG. 2.

The data in FIG. 2 clearly show a decline in the amount of mitochondrial DNA per cell with more than 2 logs and therewith the mitochondrial toxicity of the antiviral drug ddC.

Example 3

Fibroblast cells were cultured in vitro in the presence of the antiviral drugs ddC, AZT and D4T at two concentrations each, 3 μM and 30 μM, respectively, for 4 weeks. As controls, cell cultures with ethidium bromide and without drugs were also performed. Ethidium bromide is known to deplete mitochondrial DNA completely from cells and is a positive control in terms of achieving an effect on the mitochondria content of cells. At one week intervals, part of the cells was harvested and analyzed for an amount of mitochondrial RNA (primers MtR p1 and MtR p2 and probe MtR mb) and chromosome-encoded RNA (primers SnrpR p1 and SnrpR p2 and probe SnrpR mb) in the described NASBA protocol. The cultures with AZT, D4T and without additive showed no measurable change in mitochondrial RNA to chromosome-encoded RNA ratio in the culture period of 4 weeks. The culture with ethidium bromide showed a decline in mitochondrial RNA content as expected. The results for ddC are shown in FIG. 3. The data in FIG. 3 clearly show a decline in the amount of mitochondrial RNA per cell with at least 2 logs and therewith the mitochondrial toxicity of the antiviral drug ddC. The time point at 3 weeks has a very low value and presumably this is somewhat of an outlier measurement.

Example 4

Fibroblast cells were cultured in vitro in the presence of the antiviral drugs ddC, AZT and D4T at two concentrations each, 3 μM and 30 μM, respectively, for 4 weeks. As controls, cell cultures with ethidiumn bromide and without drugs were also performed, Ethidium bromide is known to deplete mitochondrial DNA completely from cells and is a positive control in terms of achieving an effect on the mitochondria content of cells. At one week intervals, part of the cells was harvested and analyzed for an amount of mitochondrial RNA (primers MtR p1 and MtR p2 and probe MtR mb) and chromosomal DNA (primers SnrpD p1 and SnrpD p2 and probe SnrpD mb) in the described NASBA protocol.

The cultures with AZT, D4T and without additive showed no measurable change in mitochondrial RNA to chromosomal DNA ratio in the culture period of 4 weeks. The culture with ethidium bromide showed a decline in mitochondrial RNA content as expected. The results for ddC are shown in FIG. 4.

The data in FIG. 4 clearly show a decline in the amount of mitochondrial RNA per cell with almost 3 logs and therewith the mitochondrial toxicity of the antiviral drug ddC. The time point at 3 weeks has a very low value and presumably this is somewhat of an outlier measurement.

Fibroblast cells were cultured in vitro in the presence of the antiviral drugs ddC, AZT and D4T at two concentrations each, 3 μM and 30 μM, respectively, for 4 weeks. As controls, cell cultures with ethidium bromide and without drugs were also performed. Ethidium bromide is known to deplete mitochondrial DNA completely from cells and is a positive control in terms of achieving an effect on the mitochondria content of cells. At one week intervals, part of the cells was harvested and analyzed for an amount of mitochondrial RNA (primers MtR p1 and MtR p2 and probe MtR mb) and mitochondrial DNA (primers MtD p1 and MtD p2 and probe MtD mb) in the described NASBA protocol.

The cultures with AZT, D4T and without additive showed no measurable change in mitochondrial RNA to mitochondrial DNA ratio in the culture period of 4 weeks. The culture with ethidium bromide showed a decline in mitochondrial RNA and DNA content as expected. The results for ddC are shown in FIG. 5.

The data in FIG. 5 clearly show that the ratio of mitochondrial DNA to RNA is not significantly changing over the period of 4 weeks. The time point at 3 weeks in FIG. 5 has a low value for mitochondrial RNA that shows up; this measurement is presumably somewhat of an outlier measurement.

Example 6

Fibroblast cells were cultured in vitro in the presence of the antiviral drugs ddC, AZT and D4T at two concentrations each, 3 μM and 30 μM, respectively, for 4 weeks. As controls, cell cultures with ethidium bromide and without drugs wee also performed. Ethidium bromide is known to deplete mitochondrial DNA completely from cells and is a positive control in terms of achieving an effect on the mitochondria content of cells. At one-week intervals, part of the cells was harvested and analyzed for an amount of chromosome-encoded RNA (primers SnrpR p1 and SnrpR p2 and probe SnrpR mb) and chromosomal DNA (primers SnrpD p1 and SnrpD p2 and probe SrpD mb) in the described NASBA protocol.

The cultures with AZT, D4T, ethidium bromide and without additive showed no measurable change in ratio in the culture period of 4 weeks. The results for ddC are shown in FIG. 6.

The data in FIG. 6 clearly show that the ratio of chromosomal DNA to RNA is not significantly changing over the period of 4 weeks.

Example 7

Fibroblast cells were cultured in vitro in the presence of the antiviral drug ddC at a concentration of 30 $\mu$M for 4 weeks. After that period, the cell culture continued but now in the absence of ddC. During this period of culture without ddC, part of the cells was harvested and analyzed for an amount of mitochondrial DNA (primers MtD p1 and MtD p2 and probe MtD mb) and chromosomal DNA (primers SnrpD p1 and SnrpD p2 and probe SnrpD mb) in the described NASBA protocol at two-week intervals for a period of 12 weeks. The results of the analysis are shown in FIG. 7.

The results in FIG. 7 clearly show that the amount of mitochondria per cell increases with more than 2 logs after ddC is removed from the culture. This result shows that the toxic effect of ddC can be reversed if there are still some mitochondria left in the cells to repopulate the new growing cells.

Example 8

Fibroblast cells were cultured in vitro in the presence of the antiviral drug ddC at a concentration of 30 $\mu$M for 4 weeks. After that period, the cell culture continued but now in the absence of ddC. During this period of culture without ddC, part of the cells was harvested and analyzed for an amount of mitochondrial RNA (primers MtR p1 and MtR p2 and probe MtR mb) and chromosome-encoded RNA (primers SnrpR p1 and SnrpR p2 and probe SnrpR mb) in the described NASBA protocol at two-weeks intervals for a period of 12 weeks. The results of the analysis are shown in FIG. 8.

The result in FIG. 8 clearly show that the amount of mitochondrial RNA per cell increases with more than 2 logs after ddC is removed from the culture. This results shows that the toxic effect of ddC can be reversed and that the function of the mitochondria comes back as shown by synthesis of RNA and, subsequently, proteins.

Example 9

Fresh peripheral blood mononuclear cells (PBMC's) from a healthy blood donor were cultured in vitro in the presence of the antiviral drugs ddC, AZT and D4T at two concentrations each, 6 $\mu$M and 60 $\mu$M, respectively, for 5 days. As controls, cell cultures with DMSO and without drugs were also performed. DMSO is part of the solvent in which the drugs are solubilized. After 5 days, the cells were harvested and analyzed for an amount of mitochondrial DNA (primers MtD p1 and MtD p2 and probe MtD mb) and chromosomal DNA (primers SnrpD p1 and SnrpD p2 and probe SnrpD mb) in the described NASBA protocol.

The cultures with AZT, D4T, DMSO and without additive showed no measurable change in ratio in the culture period of 5 days. The results for ddC are shown in FIG. 9.

The results in FIG. 9 clearly show the decline in PBMC's of mitochondrial DNA per cell of more than 1 log during the 5-day culture period.

Example 10

Fresh peripheral blood mononuclear cells (PBMC's) from a healthy blood donor were cultured in vitro in the presence of the antiviral drugs ddC, AZT and D4T at two concentrations each, 6 $\mu$M and 60 $\mu$M, respectively, for 5 days. As controls, cell cultures with DMSO and without drugs were also performed. DMSO is part of the solvent in which the drugs are solubilized. After 5 days, the cells were harvested and analyzed for an amount of mitochondrial RNA (primers MtR p1 and MtR p2 and probe MtR mb) and chromosome-encoded RNA (primers SnrpR p1 and SnrpR p2 and probe SnrpR mb) in the described NASBA protocol.

The cultures with AZT, D4T, DMSO and without additive showed no measurable change in ratio in the culture period of 5 days. The results for ddC are shown in FIG. 10. Interestingly, the results in FIG. 10 do not clearly show a decline in PBMC's of mitochondrial RNA per cell during the 5-day culture period at the highest concentration of ddC used. This is in contrast to the mitochondrial DNA as shown in example 9. Probably the decline in mitochondrial DNA is compensated by an increase in transcription, maintaining the level of mitochondrial RNA. This mechanism delays the decline of mitochondrial RNA.

Consequently, one can say that the mitochondrial RNA is a reflection of the current status of the functionality of the mitochondria and that mitochondrial DNA is predictive of what will happen in the (near) future with the mitochondrial function and therefore has a more prognostic character.

Example 11

Using the primers and probes Rubisco-DNA p1, Rubisco-DNA p2, Rubisco-DNA MB, Rubisco-RNA p1, Rubisco-RNA p2 and Rubisco-RNA-MB (table 1), the chloroplast DNA and RNA of *Oryza sativum* (rice) can be quantified and the ratio to the chromosomal DNA and RNA can be determined by using primers and probes OryzaDNA p1, OryzaDNA p2, OryzaDNA mb, OryzaRNA p1, OryzaRNA p2, OryzaRNA mb (table 1). During the application of herbicide (or other) compounds, the conditions of the plants can be assessed by measurement of the chloroplast nucleic acid content of the cells using amplification methods like PCR and NASBA that are known to persons skilled in the art. At the same time, using primer sets suitable for weeds, the deterioration of the unwanted plants can be monitored. It is clear that these molecular tools are very suited in the research for new herbicides that specifically attack one group of plants and not others.

Example 12

In this example, the NASBA nucleic acid amplification reactions for DNA target sequences were performed in a 20 $\mu$l reaction volume and contained: 4 mM Tris-pH 8.5, 70 mM KCl, 12mM $MgCl_2$, 5mM dithiotreitol, 1mM dNTP's (each), 0.2 mM rNTP's (each), 0.2 $\mu$M primer (each), 0.05 $\mu$M molecular beacon, 1.5 units restriction enzyme Msp I, 375mM sorbitol, 0.105 $\mu$g/$\mu$l bovine serum albumin, 6.4 units AMV RT, 32 units T7 RNA polymerase, 0.08 units RNAse H and input nucleic acid. The complete mixture, except the enzymes sorbitol and bovine serum albumin, was, prior to adding the enzyme mixture, incubated at 37° C. for 25 minutes and subsequently heated to 95° C. for two minutes in order to denature the DNA and to allow the primers to anneal. After cooling the mixture to 41° C., the enzyme mixture was added. The amplification took place at 41° C. for 90 min in a fluorimeter (CytoFluor 2000) and the fluorescent signal was measured every minute (using the filter set 530/25 nm and 485/30 nm). To achieve quantification, a dilution series of target sequence for a particular primer set was amplified and the time points at which the reactions became positive (the time to positivity, TTP) were plotted against the input amounts of nucleic acid. This way a calibration curve was created that could be used to read TTP values of reactions with unknown amounts of input and deduce the input amount. Fresh peripheral blood mononuclear cells (PBMC's) from a healthy blood donor were cultured in vitro for 5 days. After 5 days, the cells were harvested and analyzed for an amount of chromosomal DNA (primers SnrpD p1 and SnrpD2 p2 and probe SnrpD mb) with the described NASBA protocol in the chapter "Used ingredients and general methodology" and compared with the NASBA protocol as described in this example. As can be clearly seen in FIG. 11, the DNA NASBA reactions with pretreatment of restriction enzyme perform much better than without. The rationale for this observation is the direct extension from the Msp I created 3' over the T7 promoter part of the p1 primer.

Example 13

Using the primers and probes tRNA-L-D p1, tRNA-L-D p2, tRNA-L-D MB, petB RNA p1, petB RNA p2 and petB RNA MB (table 1), the chloroplast DNA and RNA of Oryza sativum (rice) can be quantified and the ratio to the chromosomal DNA and RNA can be determined by using primers and probes OryzaDNA p1, OryzaDNA p2, OryzaDNA mb, OryzaRNA p1, OryzaRNA p2, OryzaRNA mb (table 1). During the application of herbicide (or other) compounds, the conditions of the plants can be assessed by measurement of the chloroplast nucleic acid content of the cells using amplification methods like PCR and NASBA that are known to persons skilled in the art. At the same time, using primer sets suitable for weeds, the deterioration of the unwanted plants can be monitored. It is clear that these molecular tools are very suited in the research for new herbicides that specifically attack one group of plants and not others.

Example 14

A thousand molecules of plasmid containing Snrp DNA were mixed with $4 \times 10^5$, $2 \times 10^5$, $10^5$, $5 \times 10^4$, $2.5 \times 10^4$, or $10^4$ molecules of plasmid containing mitochondrial DNA, and the mixture was used as input for the reactions. A reaction mix was prepared similar to that of example 12, except that primers and beacons differed in order to amplify Snrp-nuclear and mitochondrial DNA in one tube. The reaction mix (duplex-mix) contained two sets of primers and beacon: SnrpD p1 and SnrpD p2, and MtD p1_2 and MtD p2_2 (each 0.2 $\mu$M) with beacons SnrpD mb (ROX-labeled) and MtD mb_2 (FAM-labeled) (each 0.05 $\mu$M). Restriction enzyme digestion, amplification, and detection were performed as in example 12. Filter sets of the fluorimeter (CytoFluor 2000) were adapted to simultaneously measure the FAM and the ROX-label (485/20 and 530/25 for FAM; 590/20 and 645/40 for ROX). In a duplex reaction with two competing amplifications, the ratio of the slope of the curves of fluorescence in time is proportional to the ratio of the amount of molecules of each amplified species (see FIG. 12).

Example 15

PBMC were cultured in the absence and presence of 5 $\mu$M ddC. After 5 days, PBMC samples were drawn. Nucleic acids were isolated from $10^5$ PBMC according to the method described by Boom et al. and dissolved in 50 $\mu$l DNAse-free and RNAse-free water. 1:10 and 1:100 dilutions were made, and 5 $\mu$l of the dilutions (equivalent to 1,000 or 100 PBMC, respectively) were put in the reaction mix to amplify the specific targets. In parallel, $10^3$ molecules of plasmid containing Snrp DNA was mixed with $4 \times 10^5$, $2 \times 10^5$, $10^5$, or $5 \times 10^4$ molecules of plasmid containing mitochondrial DNA, and the mixture was used as input for the reactions. A reaction mix was prepared similar to that of example 12, except that primers and beacons differed in order to amplify Snrp-nuclear and mitochondrial DNA in one tube The reaction mix (duplex-mix) contained two sets of primers and beacons: SnrpD p1 and SnrpD p2, and MtD p1_2 and MtD p2_2 (each 0.2 $\mu$M) with beacons SnrpD mb (ROX-labeled) and MtD mb_2 (FAM-labeled) (each 0.05 $\mu$M). Restriction enzyme digestion, amplification, and detection were performed as in example 12. Filter sets of the fluorimeter (CytoFluor 2000) were adapted to simultaneously measure the FAM and the ROX-label (485/20 and 530/25 for FAM; 590/20 and 645/40 for ROX). In a duplex reaction with two competing amplifications, the ratio of the slope of the curves of fluorescence in time is proportional to the ratio of the amount of molecules of each amplified species. The data of the plasmid Snrp/mitochondrial DNA mixtures were used to create a standard curve on which the unknown ratio of mitochondrial to Snrp nuclear DNA of the PBMC samples in the dilutions 1:10 and 1:100 in the absence and presence of 5 $\mu$M ddC could be assessed (see FIG. 13).

Example 16

From an HIV-1 infected patient that died as a result of severe lactic acidosis, 4 blood samples were analyzed for the mitochondrial content of the peripheral blood mononuclear cells (PBMC). Sample 1 was taken 1 year prior to the moment of death, sample 2 was taken 3 months before the moment of death, sample 3 was taken 1.5 months before the moment of death and sample 4 was taken just before death. The blood was used to prepare peripheral blood mononuclear cells (PBMC) by Ficoll-Isopaque purification. PBMC were viably frozen in medium plus 5% DMSO and stored in liquid nitrogen until use. Nucleic acids were extracted from $10^5$ PBMC using the Boom method. Nucleic acids equivalent of 1,000 PBMC were used as input for the NASBA that measures mitochondrial DNA (primers MtD p1 and MtD p2 and probe MtD mb) and the NASBA that measures chromosomal DNA (primers SnrpD p1 and SnrpD p2 and probe SnrpD mb). See table 1 for primer and probe sequences. The result of this assay is expressed as the mitochondrial DNA copies per chromosomal DNA copy (see FIG. 14).

Example 17

Different ratios of mitochondrial and chromosomal DNA targets in plasmids were analyzed in this example: $2 \times 10^3$ U1a DNA/$8 \times 10^3$ Mt DNA, $2 \times 10^3$ U1a DNA/$2 \times 10^4$ Mt DNA, $2 \times 10^3$ U1a DNA/$4 \times 10^4$ Mt DNA, $2 \times 10^3$ U1a DNA/$10^5$ Mt DNA, $2 \times 10^3$ U1a DNA/ $2 \times 10^5$ Mt DNA, $2 \times 10^3$ U1a DNA/$4 \times 10^5$ Mt DNA, and $2 \times 10^3$ U1a DNA/$8 \times 10^5$ Mt DNA molecules were included. A reaction mix was prepared similar to that of example 12, except that primers and beacons differed in order to amplify chromosomal and mitochondrial DNA in one tube. The reaction mix (duplex-mix) contained two sets of primers and beacons: SnrpD P1 and SnrpD2 P2 (first primer set, each 0.2 $\mu$M), and MtD P1_2 and MtD P2_2 (second primer set, each 0.3 $\mu$M) with beacons SnrpD mb_2 (FAM-labeled) and MtD mb_3 (ROX-labeled) (each 0.04 $\mu$M). See table 1 for primer and probe sequences. Restriction enzyme digestion, amplification, and detection were performed as in example 12. Filter sets of the fluorimeter (CytoFluor 2000 or EasyQ analyzer) were adapted to simultaneously measure the FAM and the ROX-label (485/20 and 530/25 for FAM; 590/20and 645/40 for ROX). In a duplex reaction with two competing amplifications, the ratio of the slope of the curves of flourescence in time is proportional to the ratio of the amount of molecules of each amplified species. The results are shown in FIG. 16. The relation between the ratio of the slopes of FAM and ROX signal is linear to the ratio of mitochondrial DNA and chromosomal DNA in the input. This result can be used to generate a calibration curve and the number of mitochondrial DNA copies per cell can be calculated from this standard calibration curve.

Example 18

Fibroblasts were cultured in the presence of the antiretroviral drug ddC (30 $\mu$M) for 4 weeks. After that period, the cell culture continued in the presence, but also in the absence, of ddC for another 6 weeks. During this period of culture, part of the cells were harvested and analyzed for the ratio of lactate-pyruvate using standard methods known by persons skilled in the art. The results of the lactate-pyruvate ratio measurements are shown in FIG. 17.

The data in FIG. 17 clearly show that in the presence of ddC, the lactate-pyruvate ratio increases, but significant increase can only be observed after 4 weeks of culture. During continued culture in the presence of ddC, the lactate-pyruvate ratio remains high; however, in continued culture after week 4 in the absence of ddC, the lactate-pyruvate ratio drops to normal levels.

Furthermore, the same samples were used to determine the ratio of mitochondrial DNA and chromosomal DNA as described in example 17. The results are shown in FIG. 18.

The data in FIG. 18 clearly show that in the presence of ddC, the fibroblasts lose their mitochondrial DNA (decline of the black line in top panels). A significant decrease in the mitochondrial DNA content can already be observed after 2 weeks and hardly any mitochondrial DNA can be observed after 3 weeks of culture in the presence of ddC. These data are in contrast to the traditional lactate-pyruvate measurements where a significant change could only be observed after 4weeks. These results clearly show the predictive value of measurement of mitochondrial DNA content for effects on functionality in time.

In the continued culture in the presence of ddC, the amount of mitochondrial DNA remains very low (bottom left two panels). Continued culture in the absence of ddC shows a clear rebound in the amount of mitochondrial DNA in the fibroblasts (bottom right two panels).

Example 19

PBMC's were cultured in the presence of the antiretroviral drug ddC (5 $\mu$M) and with a corresponding concentration of the solvent (DMSO) of the drug as a control for 11 days. During this period of culture, every two days, part of the cells were harvested and analyzed for the ratio of mitochondrial DNA and U1a DNA as described in example 17. The results are shown in FIG. 19.

The data of this experiment clearly show that the mitochondrial DNA content of PBMC in culture in the presence of ddC rapidly declines. At day two, the mitochondrial DNA content of PBMC cultured in the presence of ddC has decreased to 20%, compared to control cultures. The number or mitochondrial DNA copies in PBMC further declines to undetectable levels at day 11 of the culture in the presence of ddC.

Example 20

Forty-eight HIV-1 infected patients were randomized for antiviral therapy with either AZT, AZT+ddI, or AZT+ddC. Blood was drawn at week 0, 4, 24, and 48 after the start of therapy. The blood was used to prepare peripheral blood mononuclear cells (PBMC) by Ficoll-Isopaque purification. PBMC were viably frozen in medium plus 5% DMSO and stored in liquid nitrogen until use.

Nucleic acids were extracted from $10^5$ PBMC using the Boom method. Nucleic acids equivalent of 1,000 PBMC were used as input for the one-tube real-time duplex-NASBA that measures both mitochondrial and chromosomal DNA as described in example 17. The result of this assay is expressed as the mitochondrial DNA content per cell (i.e., PBMC) of the patient sample. The results are summarized in table 2.

The mtDNA content of the PBMC of the patients at start of therapy was compared to the mtDNA content at week 4, 24, and 48 and analyzed for statistically significant changes (see table 3 and FIGS. 20+21). The data clearly show that patients undergoing therapy containing AZT+ddI or ddC experience a significant decline in the mitochondrial DNA content of their PBMC.

Example 21

Different ratios of mitochondrial RNA target and chromosomal DNA target in a plasmid were analyzed in this example: $2\times10^3$ U1a DNA/$5\times10^4$ Mt RNA, $2\times10^3$ U1a DNA/ $2.5\times10^5$ Mt RNA, $2\times10^3$ U1a DNA/$5\times10^5$ Mt RNA, $2\times10^3$ U1a DNA/$2.5\times10^6$ Mt RNA, $2\times10^3$ U1a DNA/$5\times10^6$ Mt RNA, $2\times10^3$ U1a DNA/$10^7$ Mt RNA, $2\times10^3$ U1a DNA/ $2.5\times10^7$ Mt RNA molecules were included. A reaction mix was prepared similar to that of example 12, except that primers and beacons differed in order to amplify chromosomal DNA and mitochondrial RNA in one tube. The reaction mix (duplex-mix) contained two sets of primers and beacons: SnrpD P1 and SnrpD2 P2 (first primer set, each 0.1 $\mu$M) and MtR P1–2 and MtR P2–2 (first primer set, each 0.4 $\mu$M) with beacons SnrpD mb (ROX-labeled) and MtR mb (FAM-labeled) (each 0.04 $\mu$M). See table 1 for primer and probe sequences. Restriction enzyme digestion, amplification, and detection were performed as in example 12. Filter sets of the fluorimeter (CytoFluor 2000 or EasyQ) were adapted to simultaneously measure the FAM and the ROX-label (485/20 and 530/25 for FAM; 590/20 and 645/40 for ROX). In a duplex reaction with two competing amplifications, the ratio of the slope of the curves of fluorescence in time is proportional to the ratio of the amount of molecules of each amplified species. The results are shown in FIG. 22. The relation between the ratio of the slopes of FAM and ROX signal is linear to the ratio of mitochondrial RNA and chromosomal DNA in the input. This result can be used to generate a calibration curve and the number of mitochondrial RNA copies per cell can be calculated from this standard calibration curve.

Example 22

Fibroblasts were cultured in the presence of the antiretroviral drug ddC(30 $\mu$M) for 8 weeks. After that period, the cell culture continued in the presence, but also in the absence, of ddC for another 8 weeks. During this period of culture, part of the cells were harvested at different timepoints and analyzed for the ratio of mitochondrial RNA and chromosomal DNA as described in example 21. The results are shown in FIG. 23.

The data in FIG. 23 clearly show that in the presence of ddC, the fibroblasts lose their mitochondrial RNA. In the continued culture in the presence of ddC, the amount of mitochondrial RNA remains very low. Continued culture in the absence of ddC shows a clear rebound in the amount of mitochondrial RNA in the fibroblasts (week 10, 12, 14 and 16 timepoints).

Example 23

Two HIV-1 infected patients (patient 1 and 2)treated with antiviral therapy (AZT+ddI) were analyzed for the mitochondrial RNA content in their PBMC. Blood was drawn at week 0, 4, 24, and 48 after the start of therapy. The blood was used to prepare peripheral blood mononuclear cells (PBMC) by Ficoll-Isopaque purification. PBMC were viably frozen in medium plus 5% DMSO and stored in liquid nitrogen until use.

Nucleic acids were extracted from $10^5$ PBMC using the Boom method. Nucleic acids equivalent of 1,000 PBMC were used as input for the one-tube real-time duplex-NASBA that measures both mitochondrial RNA and chromosomal DNA as described in example 21. The result of this assay is expressed as the mitochondrial RNA content per cell (i.e., PBMC) of the patient sample. The results are summarized in table 4.

The mitochondrial RNA content of the PBMC of the patients 1 and 2 does not seem to vary significantly in the time of this study and with the therapies (drugs and doses) applied. The current study will be expanded to encompass more individuals and different therapies to get an even better assessment of the changes in mitochondrial RNA caused by therapies encompassing nucleoside analogues.

TABLE 1

Sequences of primers and probes used in the examples

| Name | Sequence[1] | |
|---|---|---|
| MtD p1 | 5' *AATTCTAATACGACTCACTATAGGG*AGAAGAGCCGTTGAGTTGTGGTA 3' | (SEQ. ID. NO. 1) |
| MtD p2 | 5' TCTCCATCTATTGATGAGGGTCTTA 3' | (SEQ. ID. NO. 2) |
| MtD mb | 5' GCATGCCCCTCCTAGCCTTACTACTAATGCATGC | (SEQ. ID. NO. 3) |
| MtD p1_2 | *AAT TCT AAT ACG ACT CAC TAT AGG* GAA GAA CCG GGC TCT GCC ATC TTA A | (SEQ. ID. NO. 4) |
| MtD p2_2 | GTA ATC CAG GTC GGT TTC TA | (SEQ. ID. NO. 5) |
| MtD mb_2 | GGA CCC CCC ACA CCC ACC CAA GAA CAG GGT CC | (SEQ. ID. NO. 6) |
| SnrpD p1 | 5' *AATTCTAATACGACTCACTATAGGG*AGAGGCCCGGCATGTGGTGCATAA 3' | (SEQ. ID. NO. 7) |
| SnrpD p2 | 5' TTCCTTACATCTCTCACCCGCTA 3' | (SEQ. ID. NO. 8) |
| SnrpD mb | 5' GCATGCTGTAACCACGCACTCTCCTCGCATGC 3' | (SEQ. ID. NO. 9) |
| SnrpD2 p2 | 5' TGCGCCTCTTTCTGGGTGTT 3' | (SEQ. ID. NO. 10) |
| MtR p1 | 5' *AATTCTAATACGACTCACTATAGGG*AGGAGAAGATGGTTAGCTCTAC 3' | (SEQ. ID. NO. 11) |
| MtR p2 | 5' CGATATGGCGTTCCCCCGCATAAA 3' | (SEQ. ID. NO. 12) |
| MtR mb | 5' GCTCCG AAGCTTCTGACTCTTACCTCCC CGGAGC 3' | (SEQ. ID. NO. 13) |
| MtR p1_2 | *AAT TCT AAT ACG ACT CAC TAT AGG* GAG AGG AGA CAC CTG CTA GGT GT | (SEQ. ID. NO. 14) |
| MtR p1_3 | *AAT TCT AAT ACG ACT CAC TAT AGG* GAG AAG GGT AGA CTG TTC AAC CTG TT | (SEQ. ID. NO. 15) |
| MtR p2_2 | GGT GCC CCC GAT ATG GCG TTC C | (SEQ. ID. NO. 16) |
| MtR p2_3 | GTA ATA ATC TTC TTC ATA GTA A | (SEQ. ID. NO. 17) |
| SnrpR p1 | 5' AATTCTAATACGACTCACTATAGGG AGAGGCCCGGCATGTGGTGCATAA 3' | (SEQ. ID. NO. 18) |
| SnrpR p2 | 5' CAGTATGCCAAGACCGACTCAGA 3' | (SEQ. ID. NO. 19) |
| SnrpR mb | 5' CGTACGAGAAGAGGAAGCCCAAGAGCCACGTACG 3' | (SEQ. ID. NO. 20) |
| SnrpR p1_2 | *AAT TCT AAT ACG ACT CAC TAT AGG* G A GAA GAA GAT GAC AAA GGC CTG GCC | (SEQ. ID. NO. 21) |
| SnrpR p1_3 | *AAT TCT AAT ACG ACT CAC TAT AGG* G A GAA AAA GGC CTG GCC CCT CAT CTT | (SEQ. ID. NO. 22) |
| SnrpR p2_2 | TCC ATG GCA GTT CCC GAG A | (SEQ. ID. NO. 23) |
| SnrpR p2_3 | CAC TAT TTA TAT CAA CAA CC | (SEQ. ID. NO. 24) |
| SnrpR p2_4 | TCA ATG AGA AGA TCA AGA A | (SEQ. ID. NO. 25) |
| SnrpR mb_2 | CGA TCG AGT CCC TGT ACG CCA TCT TC CGA TCG | (SEQ. ID. NO. 26) |
| Rubisco-DNA p1 | 5' *AATTCTAATACGACTCACTATAGGGG*ATAATTTCATTACCTTCACGAG 3' | (SEQ. ID. NO. 27) |
| Rubisco-DNA p2 | 5' GGAGTCCTGAACTAGCCGCAG 3' | (SEQ. ID. NO. 28) |
| Rubisco-DNA MB | 5' GCATGCGGTAGATAAACTAGATAGCTAGGGCATGC 3' | (SEQ. ID. NO. 29) |
| Rubisco-RNA p1 | 5' *AATTCTAATACGACTCACTATAGGGG*AGTTGTTGTTATTGTAAGTC 3' | (SEQ. ID. NO. 30) |
| Rubisco-RNA p2 | 5' CAAGTCTTATGAATTCCTATAG 3' | (SEQ. ID. NO. 31) |
| Rubisco-RNA-MB | 5' GCTAGCACACAGGGTGTACCCATTATGCTAGC 3' | (SEQ. ID. NO. 32) |
| OryzaDNA p1 | 5' *AATTCTAATACGACTCACTATAGGGG*GGATCTTAATTACATGCCGTTCA 3' | (SEQ. ID. NO. 33) |
| OryzaDNA p2 | 5' AAAGGTGCCGGTTCTCACTA 3' | (SEQ. ID. NO. 34) |
| OryzaDNA mb | 5' GCTAGCCTCTGCAAGCTTCATCAGTAATAGGGCTAGC 3' | (SEQ. ID. NO. 35) |
| OryzaRNA p1 | 5' *AATTCTAATACGACTCACTATAGGGG*CTAATGCCCTTTTCTTTTCTTCCTC 3' | (SEQ. ID. NO. 36) |
| OryzaRNA p2 | 5' CATATTGGCT TTCGAAGATT 3' | (SEQ. ID. NO. 37) |
| OryzaRNA mb | 5' GCTAGCCTTCAGCCATTATTCAAGAT GGTGCTAGC 3' | (SEQ. ID. NO. 38) |
| tRNA-L-D p1 | 5' *AATTCTAATACGACTCACTATAGGGGG*GTTCTAGTTCGAGAACCGCTTG 3' | (SEQ. ID. NO. 39) |
| tRNA-L-D p2 | 5' GCGAAATCGGTAGACGCTACG 3' | (SEQ. ID. NO. 40) |
| tRNA-L-D MB | 5' GCTAGCCAACTTCCAAATTCAGAGAAGCTAGC 3' | (SEQ. ID. NO. 41) |
| petB RNA p1 | 5' AATTCTAATACGACTCACTATAGGGAAAACCGGTAGCAACTTGTACTAG 3' | (SEQ. ID. NO. 42) |
| petB RNA p2 | 5' GGTTTCGGTATCTCTGGAATATGAG 3' | (SEQ. ID. NO. 43) |
| petB RNA MB | 5' GCTAGCGAGGAACGTCTTGAGATTCAGCTAGC 3' | (SEQ. ID. NO. 44) |
| SnrpD mb_2 | CGCATGC TGTAACCACGCACTCTCCTC GCATGCG | (SEQ. ID. NO. 45) |
| MtD mb_3 | CGTACG TGATATCATCTCAACTTAGTAT CGTACG | (SEQ. ID. NO. 46) |

[1]The T7 promoter part of primer p1 sequences is shown in *italics*, the stem sequences of the molecular beacon probes are shown in bold. The molecular beacon sequences were labelled at the 3' end with DABCYL (the quencher) and at the 5' end with 6-FAM (the fluorescent label).

TABLE 2

Mitochondrial DNA content in PBMC of patients undergoing different therapy regimens during 48 week follow up.

| | Week | Median | Interquartiles range |
|---|---|---|---|
| AZT | 0 | 196 | 111–252 |
| | 4 | 157 | 103–191 |
| | 24 | 182 | 123–224 |
| | 48 | 155 | 110–224 |
| AZT/ddI | 0 | 174 | 150–243 |
| | 4 | 126 | 89–235 |
| | 24 | 93 | 42–200 |
| | 48 | 112 | 66–170 |
| AZT/ddC | 0 | 132 | 83–200 |
| | 4 | 48 | 36–76 |
| | 24 | 68 | 29–107 |
| | 48 | 74 | 51–83 |

TABLE 3

Analysis of significant changes in mitochondrial DNA content of PBMC of patients undergoing different regimens of therapy

| Antiviral drugs | Week | % decrease | p-value |
|---|---|---|---|
| AZT | 4 | 11% | 0.22 |
|  | 24 | 1% | 0.80 |
|  | 48 | 5% | 0.55 |
| AZT + ddI | 4 | 13% | 0.04 |
|  | 24 | 24% | 0.09 |
|  | 48 | 16% | 0.02 |
| AZT + ddC | 4 | 22% | 0.002 |
|  | 24 | 22% | 0.06 |
|  | 48 | 25% | 0.04 |

TABLE 4

Mitochondrial RNA content in PBMC of patients undergoing different therapy regimens during 48 week follow up.

| Week | Patient 1 | Patient 2 |
|---|---|---|
| 0 | 632 | 680 |
| 4 | 1482 | 605 |
| 24 | 516 | 1106 |
| 48 | 448 | not valid |

TABLE 5

Mitochondrial toxicities of nucleoside and nucleotide analogue HIV-1 RT-inhibitors. From: A. Carr, DA Cooper. Lancet 2000; 356; 1423–1430

| Affected organ | Clinical features | Laboratory features | Rate (%) | Drug(s) |
|---|---|---|---|---|
| Muscle | Fatigue, myalgia, proximal weakness, wasting | Creatine kinase↑ | 17 | AZT |
| Heart | Dilated cardiomyopathy |  | Rare | AZT |
| Nerve | Distal pain, numbness, paraesthesia, reduced, reflexes/power |  | 10–30 | ddC = d4T > ddI > 3TC |
| Liver | Hepatomegaly, nausea, ascites, oedema, dyspnea, encephalopathy | Lactic acidosis Serum lactate↑ Liver enzymes↑ Anion gap↓ Bicarbonate↑ | <1 | All except, 3TC, ABC |
| Pancreas | Abdominal pain | Amylase | <1–6 | ddI > 3TC/ddC |
| Fat | Peripheral atrophy Lipodystrophy |  | 50 | d4T > others |

BRIEF DESCRIPTION OF THE DRAWINGS

FIG. 15 B. The left panel shows the lactate-pyruvate ratio's of the PBMC samples number 1 4. No increase in lactate-pyruvate ratio can be measured in these PBMC. The right panel shows the mitochondrial DNA content of PBMC in samples 1 to 4. In this experiment a clear decrease in mitochondrial DNA content can be observed.

Figure 1:
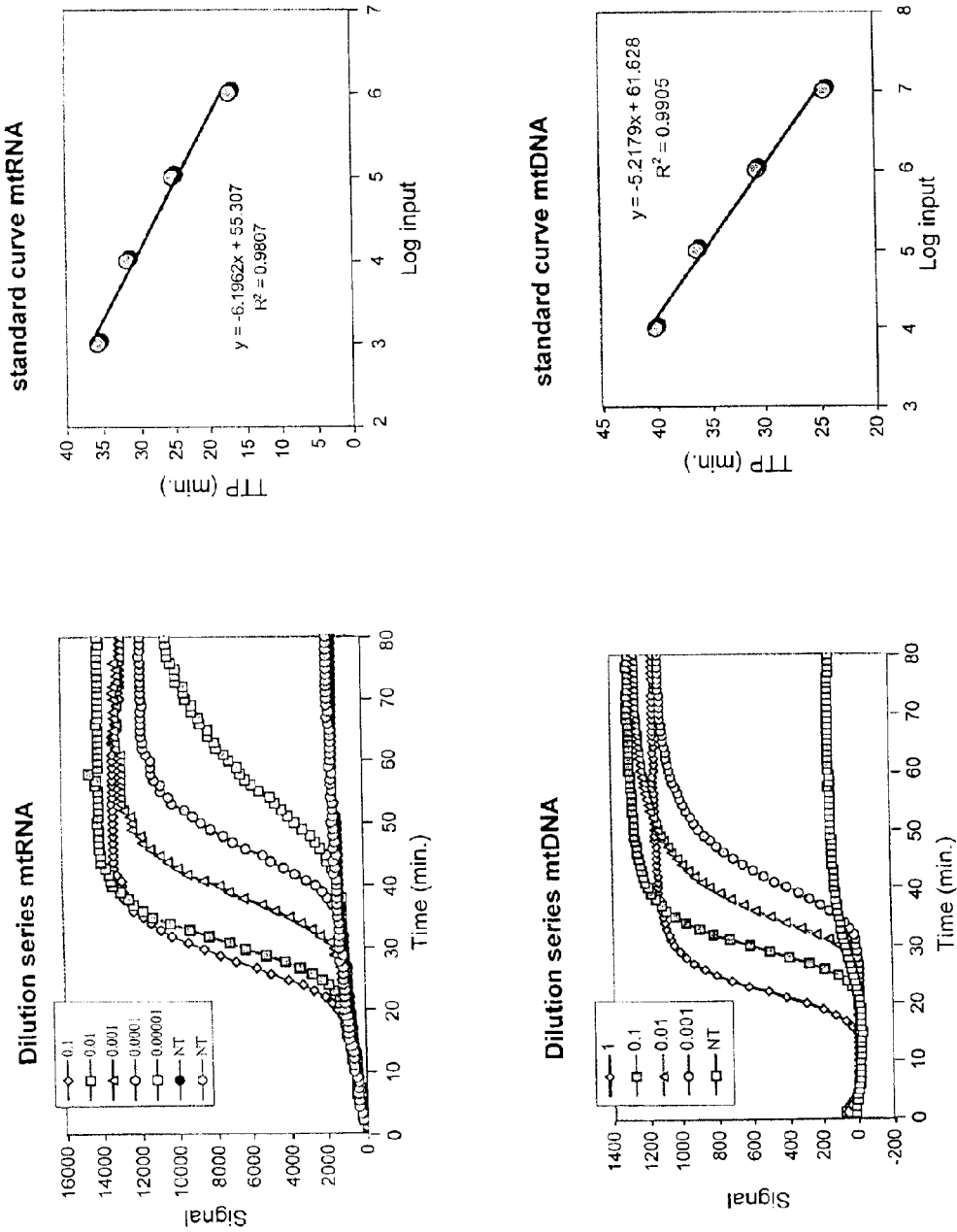
FIG. 1. Examples of standard curves for DNA and RNA target sequences.
Figure 2:
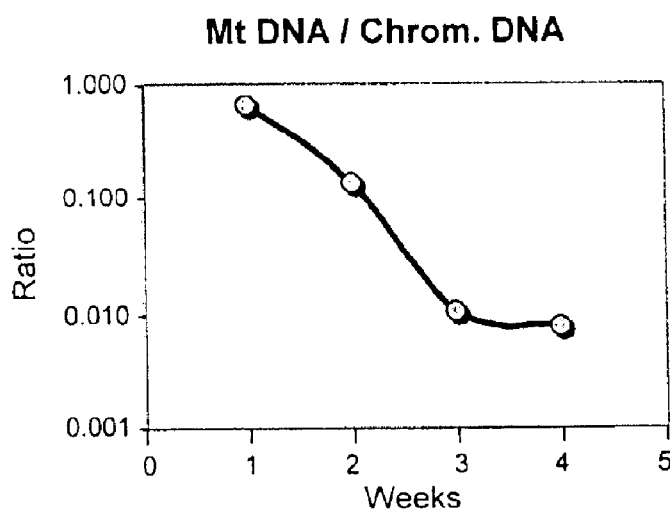
FIG. 2. Ratio of mitochondrial DNA and chromosomal DNA in fibroblast cells cultured in the presence of ddC.
Figure 3:
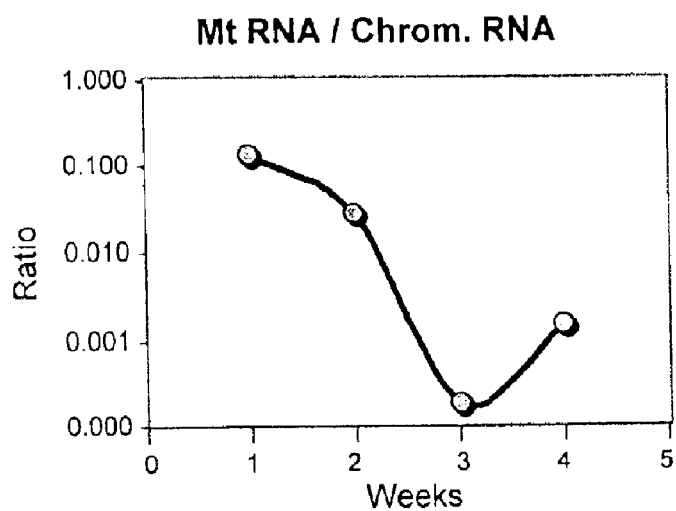
FIG. 3. Ratio of mitochondrial RNA and chromosome-encoded RNA in fibroblast cells cultured in the presence of ddC.
Figure 4:
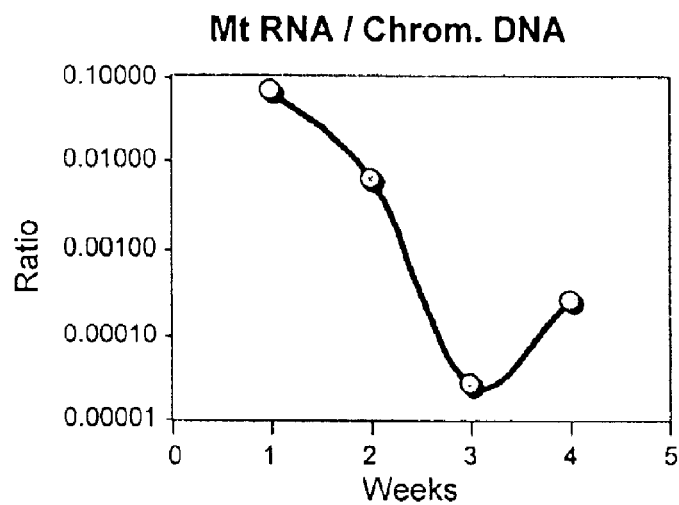
FIG. 4. Ratio of mitochondrial RNA and chromosomal DNA in fibroblast cells cultured in the presence of ddC.
Figure 5:
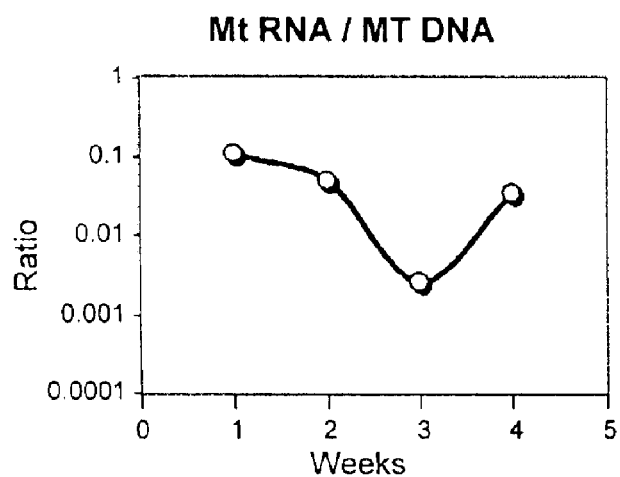
FIG. 5. Ratio of mitochondrial RNA mitochondrial DNA in fibroblast cells cultured in the presence of ddC.
Figure 6:
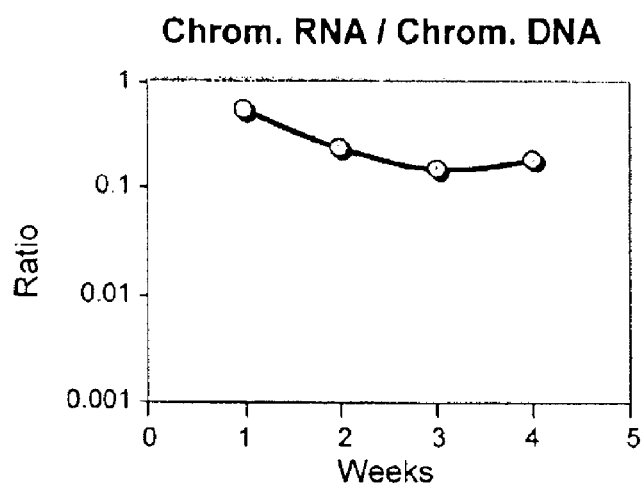
FIG. 6. Ratio of chromosome encoded RNA and chromosomal DNA in fibroblast cells cultured in the presence of ddC.
Figure 7:
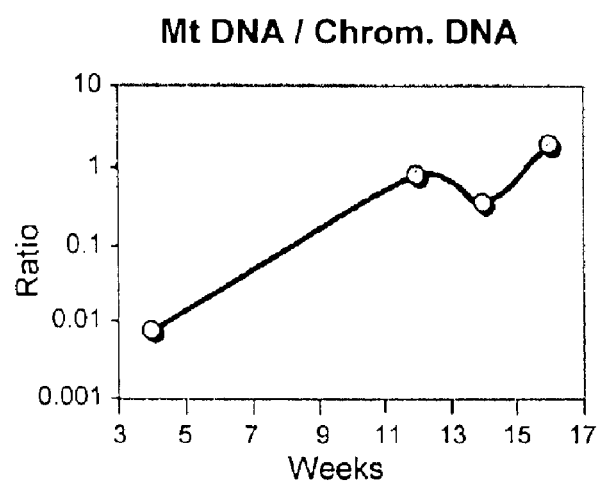
FIG. 7. Ratio of mitochondrial DNA and chromosomal DNA in fibroblast cells cultured in the absence of ddC after being cultured with ddC for 4 weeks.
Figure 8:
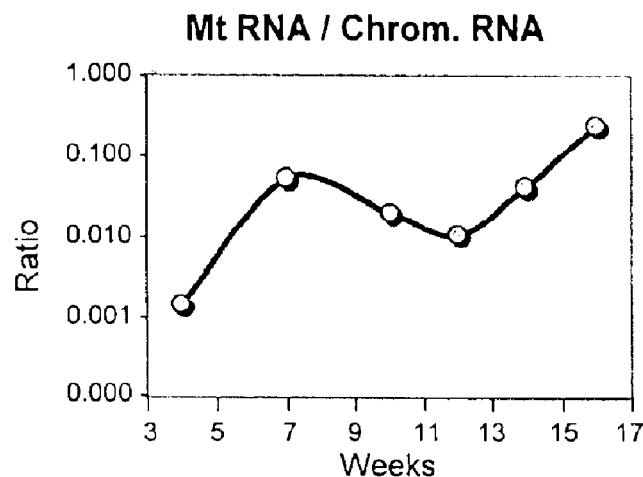
FIG. 8. Ratio of mitochondrial RNA and chromosome-encoded RNA in fibroblast cells cultured in the absence of ddC after being cultured with ddC for 4 weeks.
Figure 9:
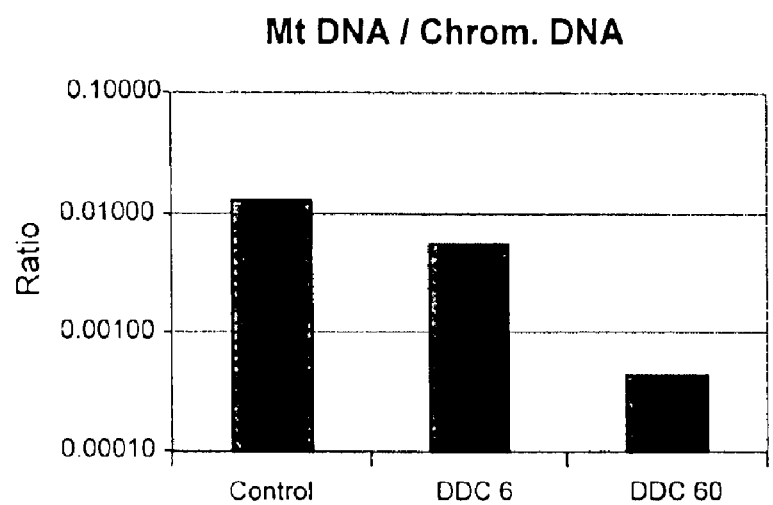
FIG. 9. Ratio of mitochondrial DNA and chromosomal DNA in PBMC's cultured in the presence of ddC for 5 days.
Figure 10:
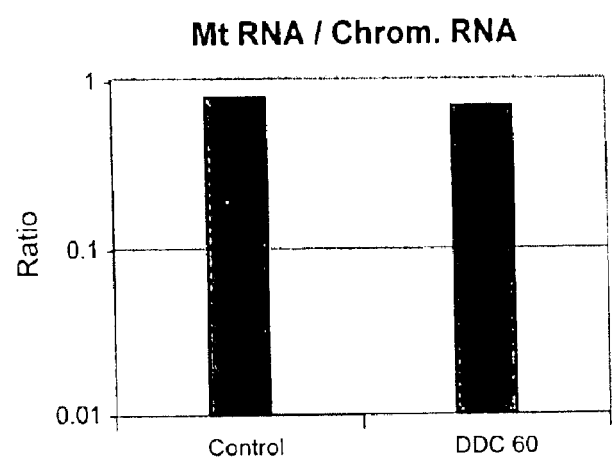
FIG. 10. Ratio of mitochondrial RNA and chromosome-encoded RNA in PBMC's cultured in the presence of ddC for 5 days.
Figure 11:
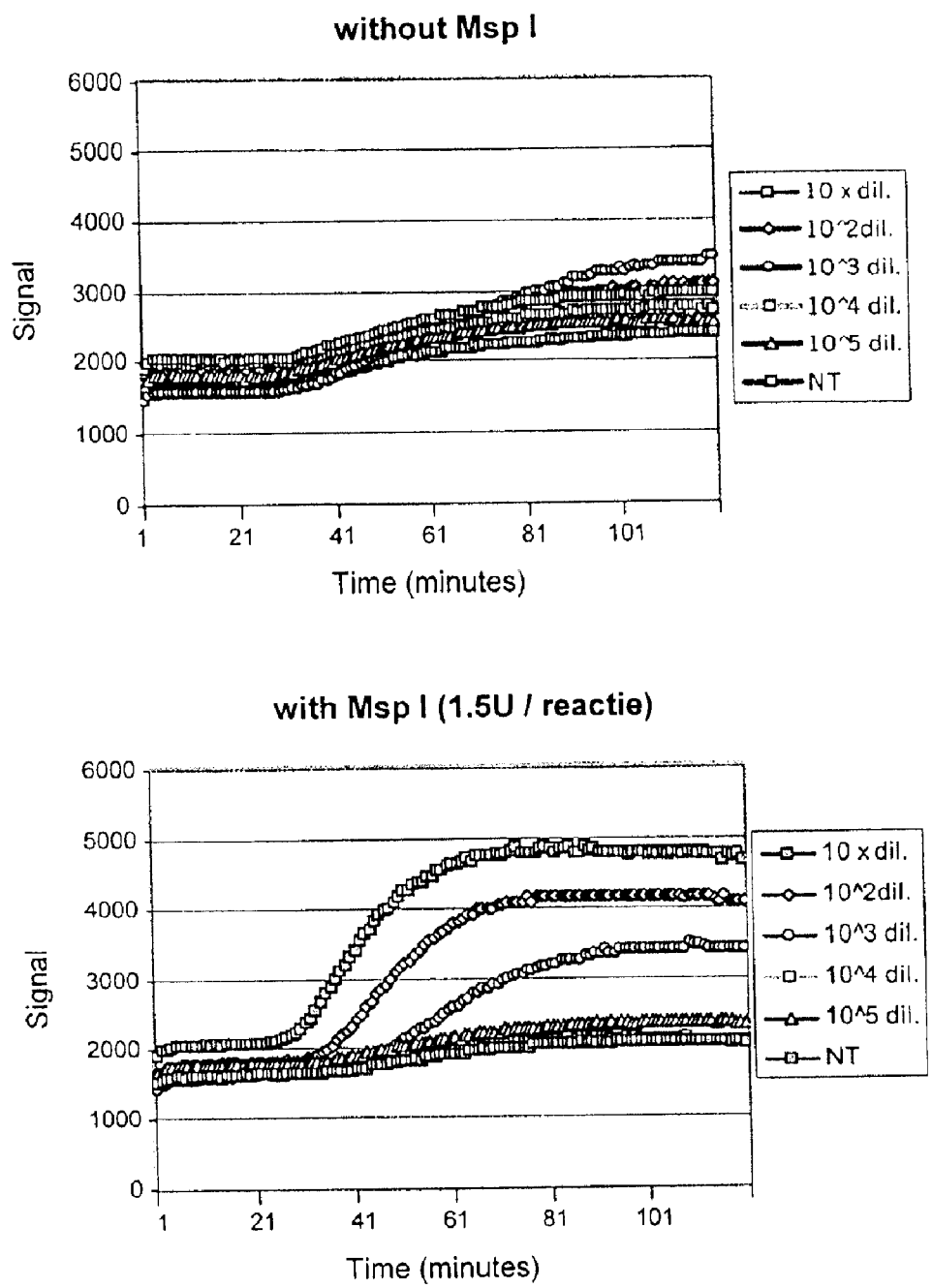
FIG. 11. Comparison of SNRNP DNA NASBA reactions with and without pretreatment with restriction enzyme Msp I.
Figure 12:
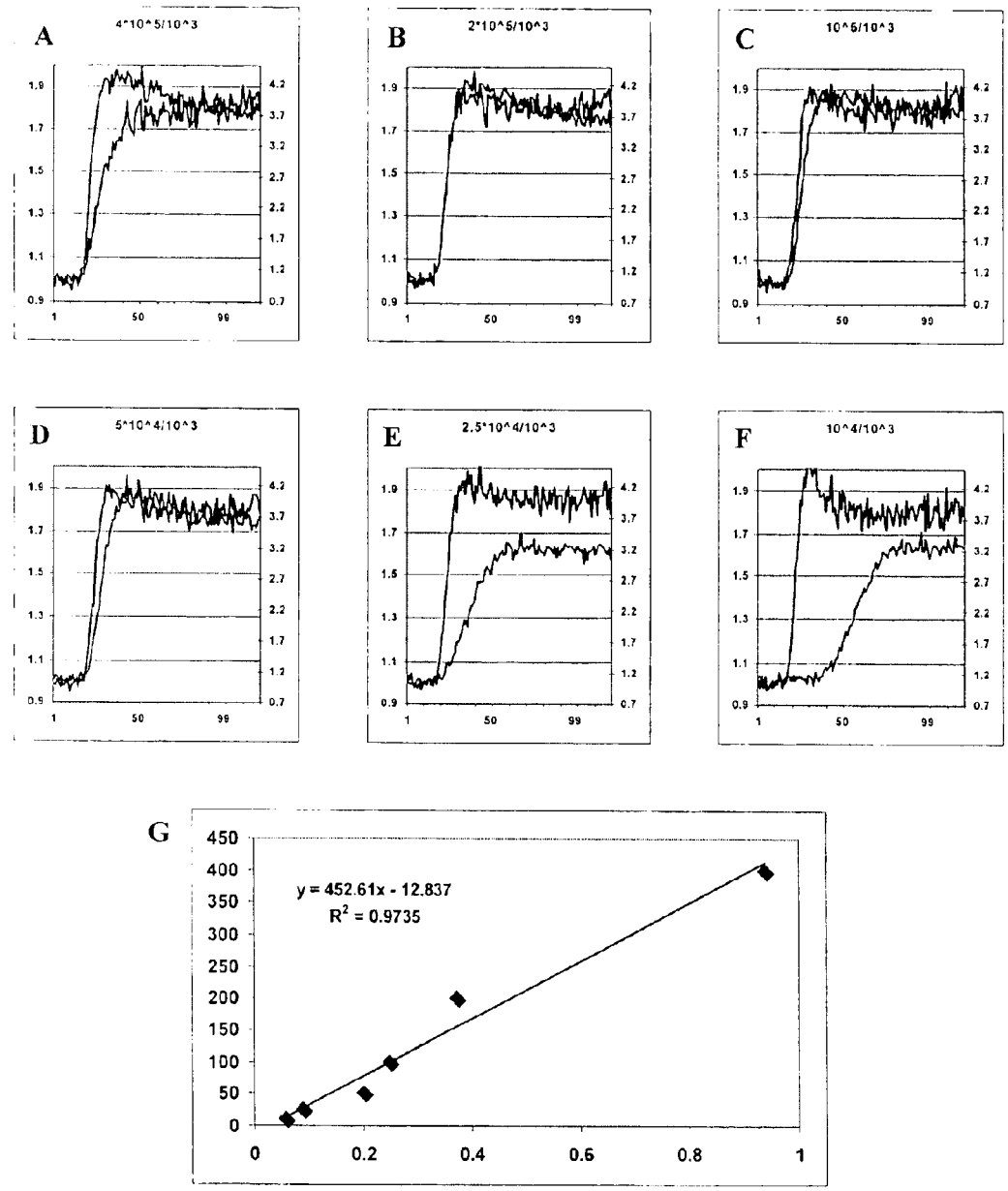
FIG. 12. Fluorescence in time of the reactions of 1000 molecules plasmid containing Snrp DNA mixed with $4 \times 10^5$ (A), $2 \times 10^5$ (B), $10^5$ (C), $5 \times 10^4$ (D), $2.5 \times 10^4$ (E) or $10^4$ (F) molecules of plasmid containing mitochondrial DNA. The curve (G) of the ratio of the amount of molecules of amplified mitochondrial DNA to Snrp nuclear DNA plotted against the ratio of the slope of the corresponding fluorescence in time.
Figure 13:
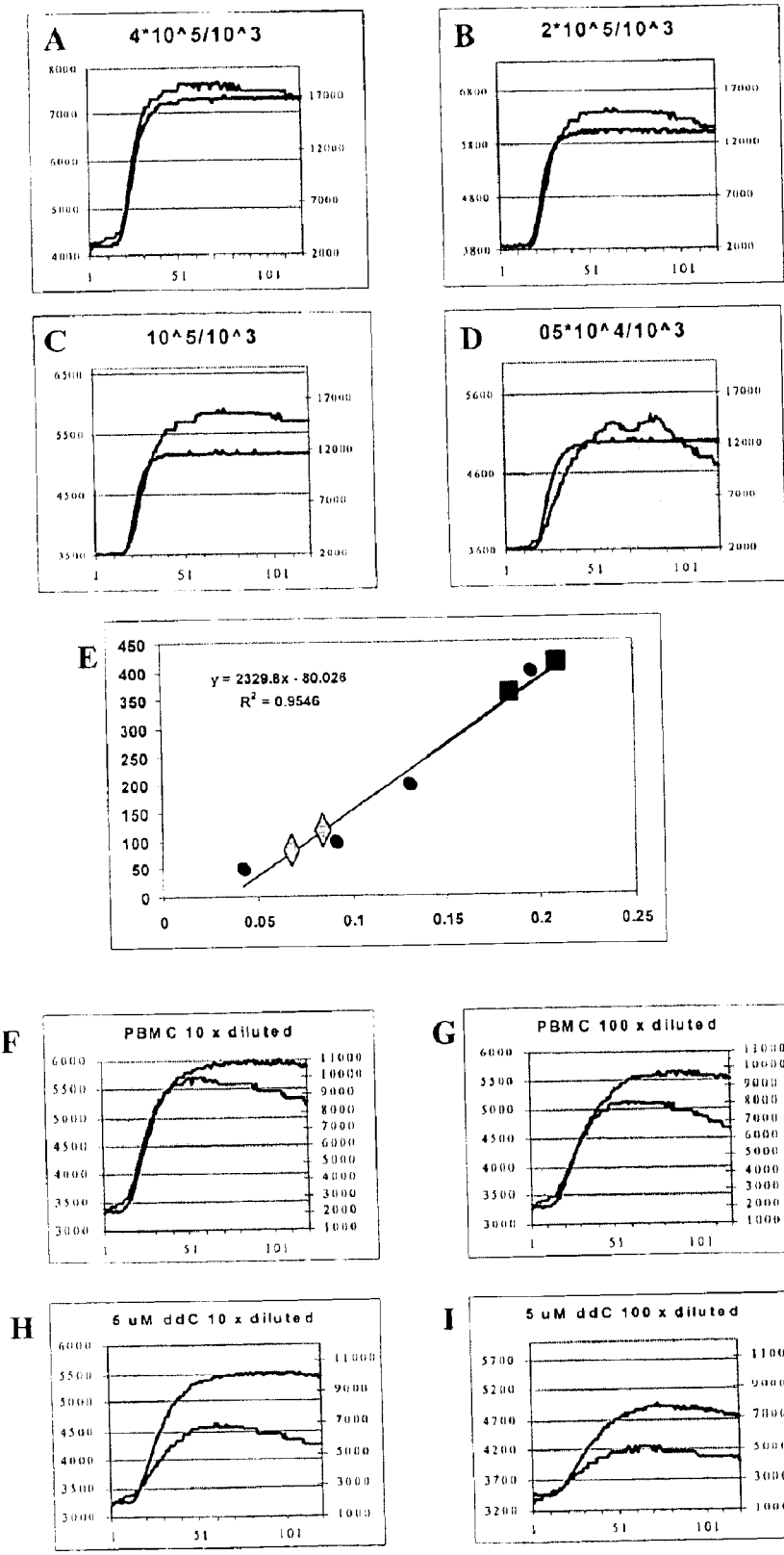
FIG. 13. Fluorescence in time of the reactions of 1000 molecules plasmid containing Snrp DNA mixed with $4 \times 10^5$ (A), $2 \times 10^5$ (B), $10^5$ (C), or $5 \times 10^4$ (D) molecules of plasmid containing mitochondrial DNA. The standard curve (E) of the ratio of the amount of molecules of amplified plasmid mitochondrial DNA to plasmid Snrp nuclear DNA plotted against ratio of the slope of the corresponding fluorescence in time as derived from the figures A-D; closed circles indicate data points. The 1:10 (F, H) and 1:100 (G,I) dilutions of PBMC in the absence (F, G) and the presence of 5 $\mu$M ddC (H, I). In FIG. E, the squares represent the PBMC samples cultured in the absence of ddC and the diamonds represent PBMC samples cultured in the presence of 5 $\mu$M ddC.
Figure 14:
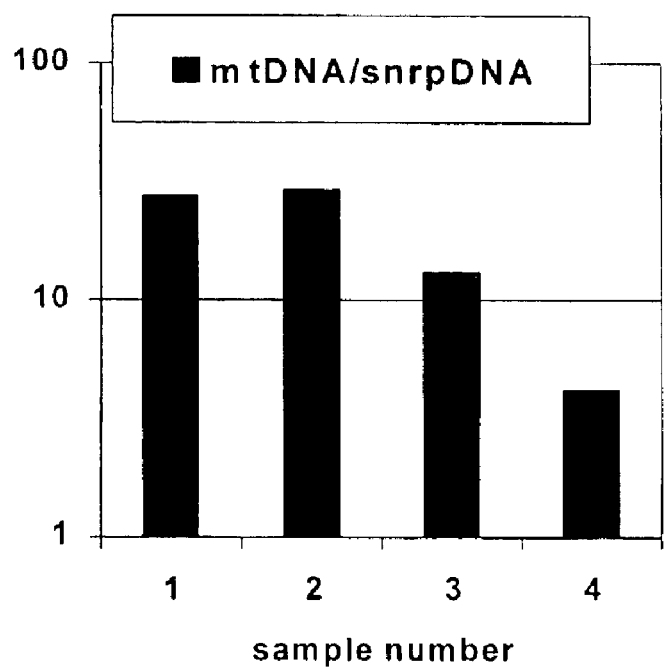
FIG. 14. Mitochondrial DNA copies per chromosomal DNA copy in four blood PBMC samples of an HIV-1 infected patient that died of lactic acidosis. For further explanation of time points see text.
Figure 15A:
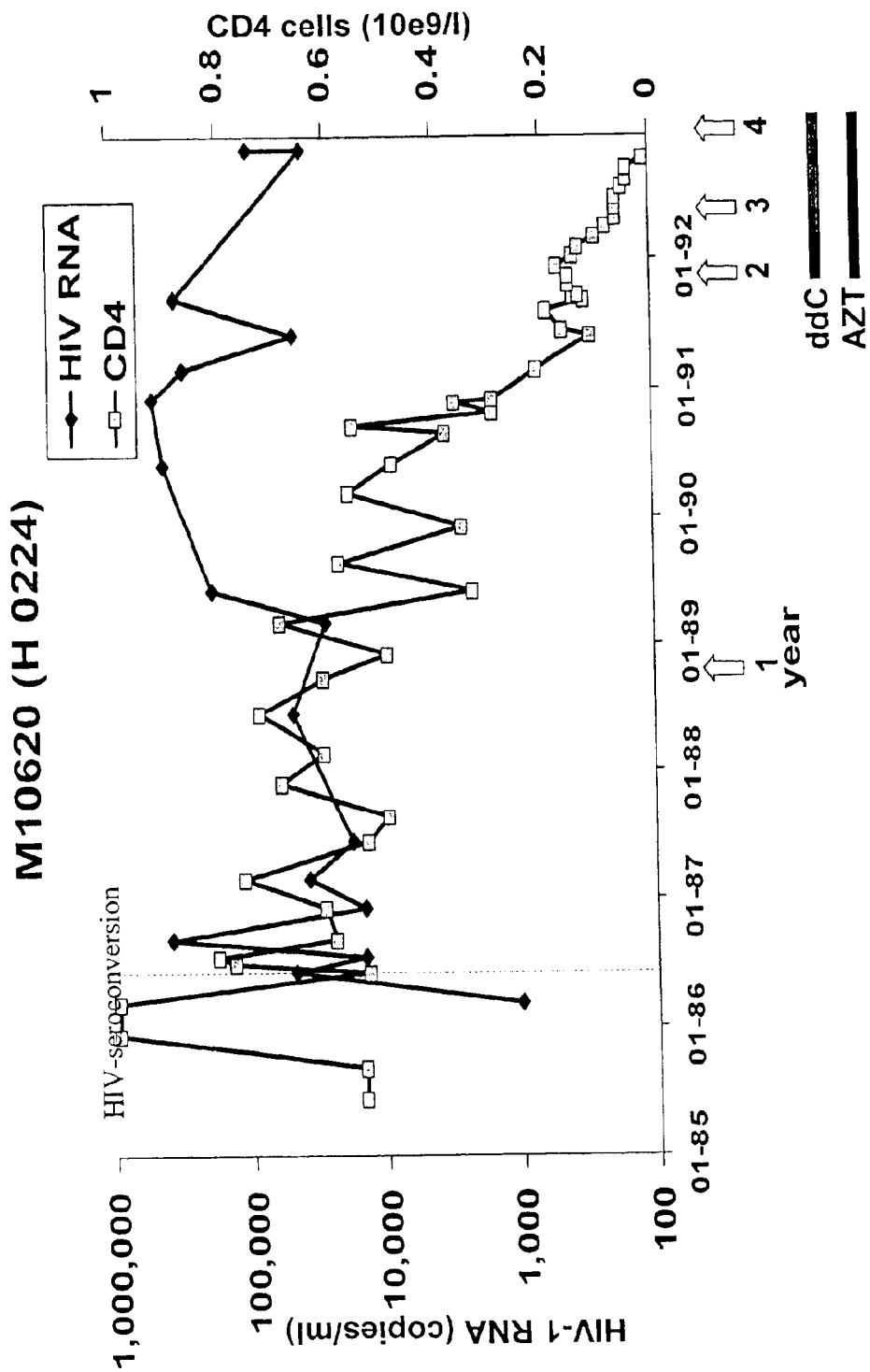
FIG. 15 A. CD4 positive cell numbers and HIV-1 RNA load of an HIV-1 infected individual. Bars labeled With ddC and AZT below the X-axis indicate the time period of treatment with these drugs. The 4 arrows below the X-axis indicate the time points at which samples of PBMC were analyzed for mitochondrial DNA content and lactate-pyruvate ratio. Approximately one month after time point 4, the patient died of lactate-acidosis.
Figure 15B:
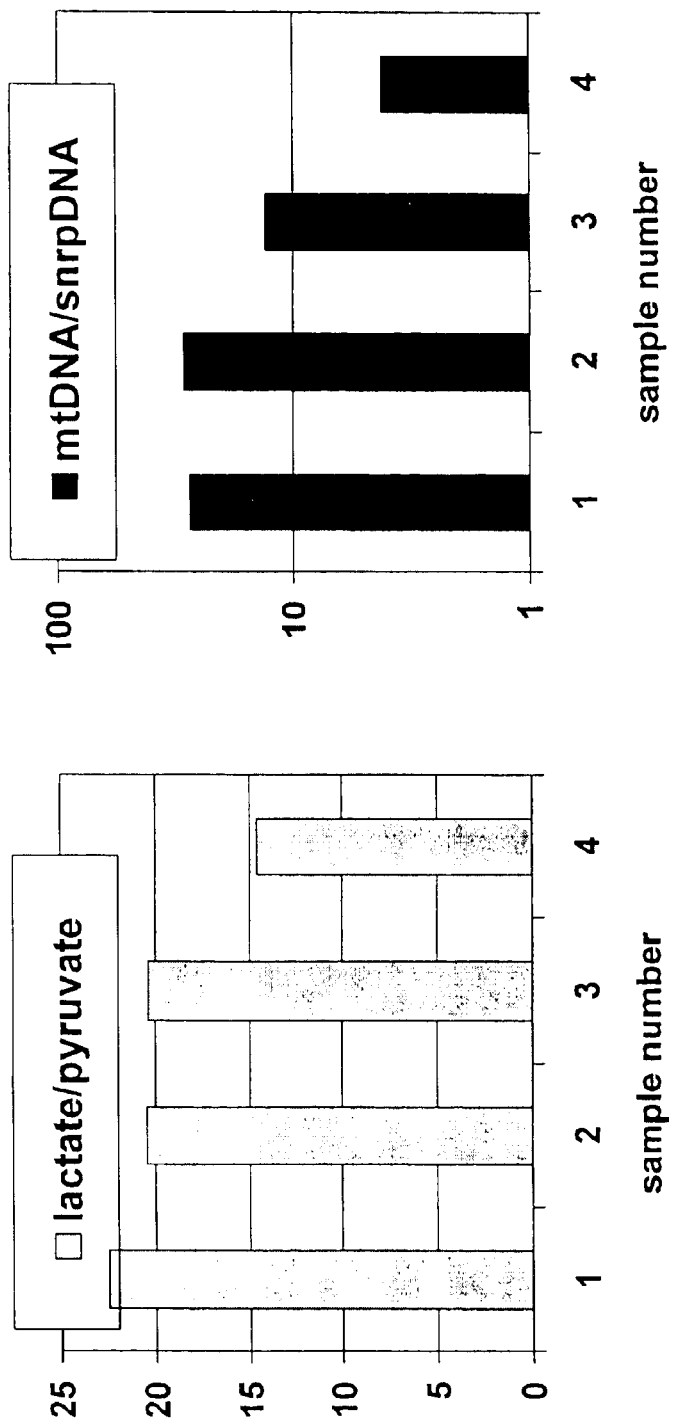
Figure 16:
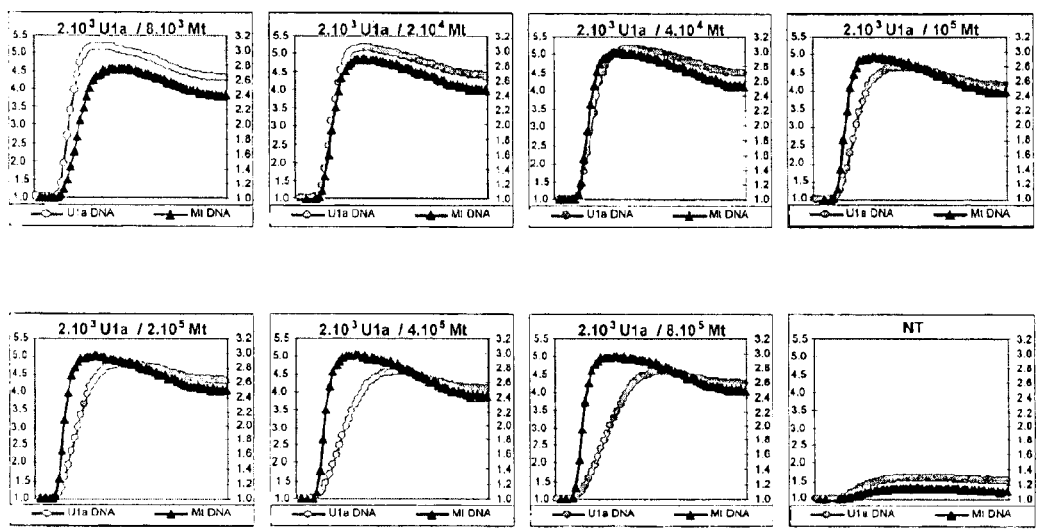
FIG. 16. Fluorescence in time of ROX (chromosomal DNA, grey lines) and FAM (mitochondrial DNA, black lines) fluorescent signal using different ratios of mitochondrial DNA to chromosomal DNA as input. In the lower panel the linear relation between the ratio of signal and the ratio of DNA's is shown.
Figure 16:
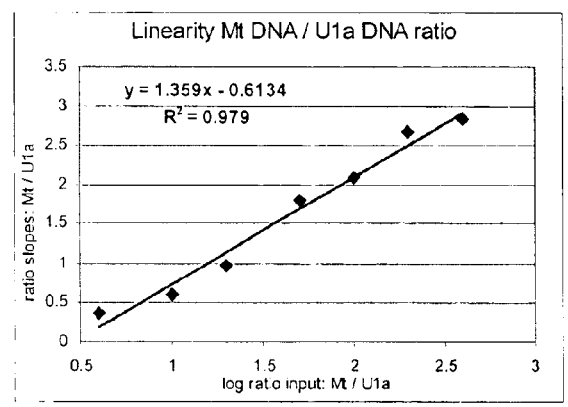
Figure 17:
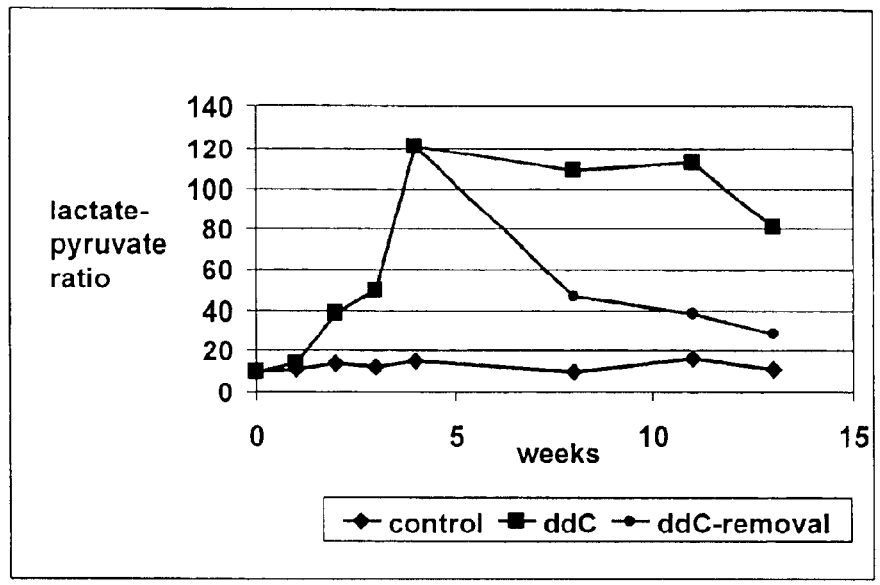
FIG. 17. Lactate-pyruvate ratio as measured in fibroblasts cultured in the presence of ddC for the first 4 weeks, after which the culture was continued both in the presence and absence of ddC.
Figure 18:
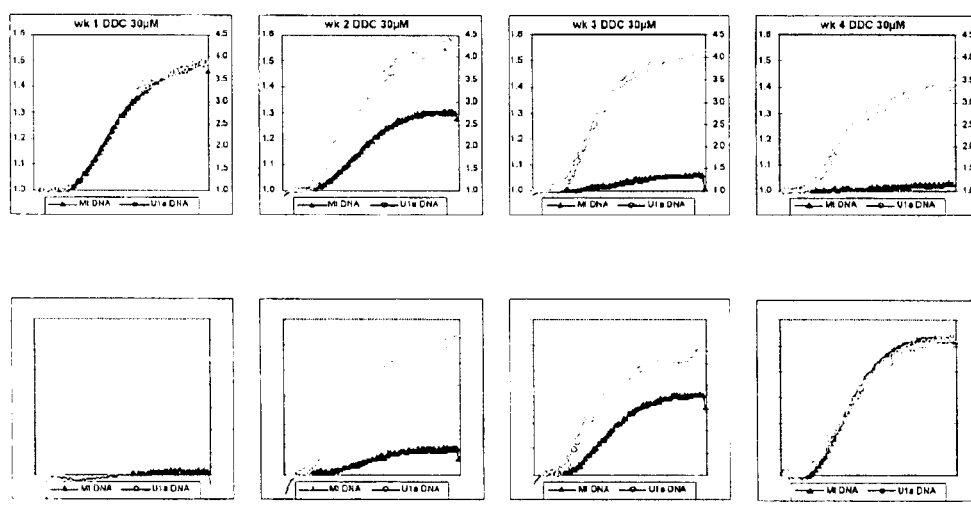
FIG. 18. Fluorescence in time of ROX (chromosomal DNA, grey lines) and FAM (mitochondrial DNA, black lines) fluorescent signal of fibroblasts cultured in the presence of ddC. Panels from top left to top right: culture in the presence of ddC for respectively 1, 2 , 3 and 4 weeks. Bottom left two panels: culture continued in the presence of ddC to respectively week 7 and week 10. Bottom right two panels: culture continued in the absence of ddC to respectively week 7 and week 10
Figure 19:
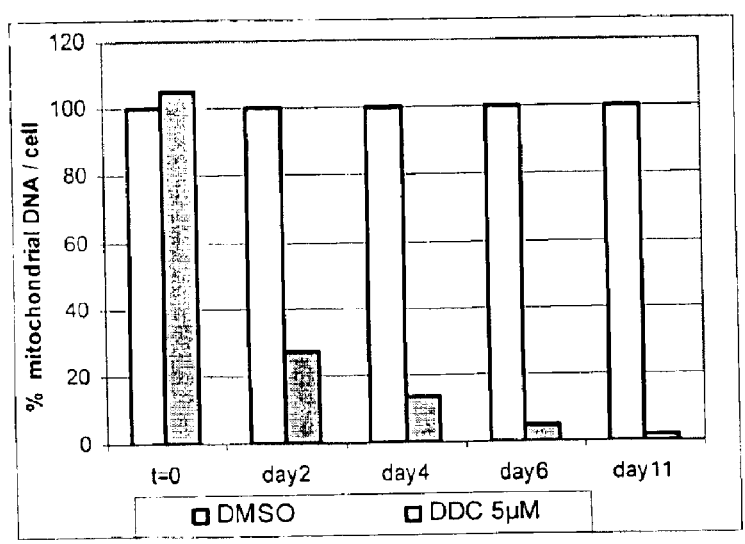
FIG. 19. The bars represent the percent of mitochondria in PBMC during culture in the absence (dotted bars) and presence (striped bars) of ddC. The amount of mitochondrial DNA in the controls (DMSO) is set at 100% at each given time point.
Figure 20:
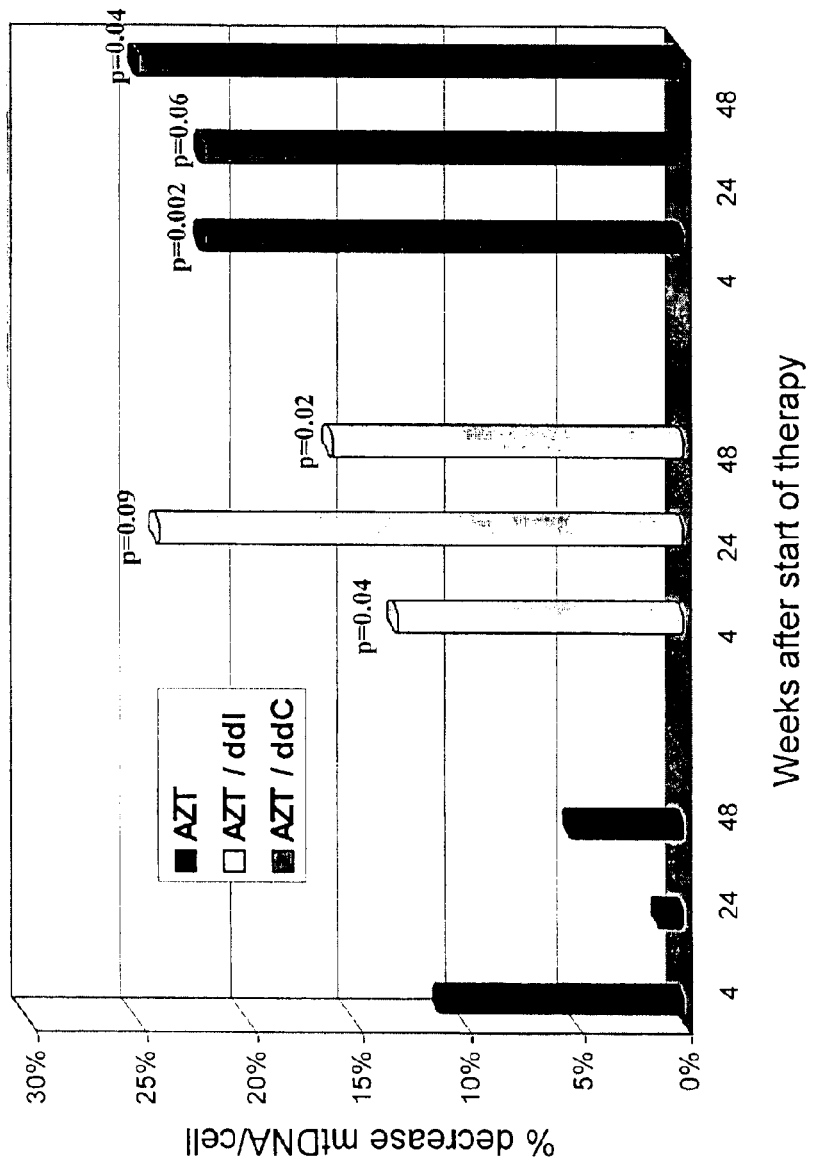
FIG. 20. Decrease of mitochondrial DNA content in 3 patient groups treated with AZT, AZT +ddI and AZT +ddC, respectively. P-values above the bars indicate significant changes in mitochondrial DNA content compared to time point zero, the start of therapy.
Figure 21:
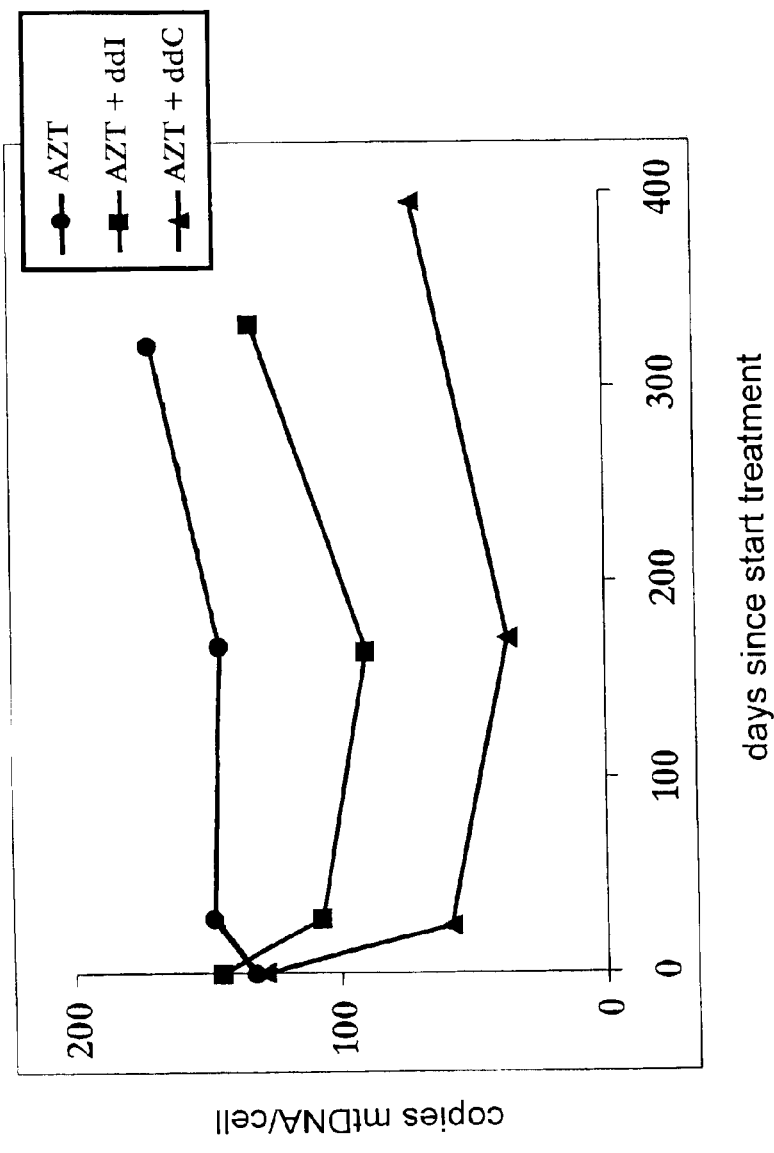
FIG. 21. The mitochondrial DNA content of 3 individual patients during treatment with AZT, AZT +ddI and AZT +ddC, respectively.
Figure 22:
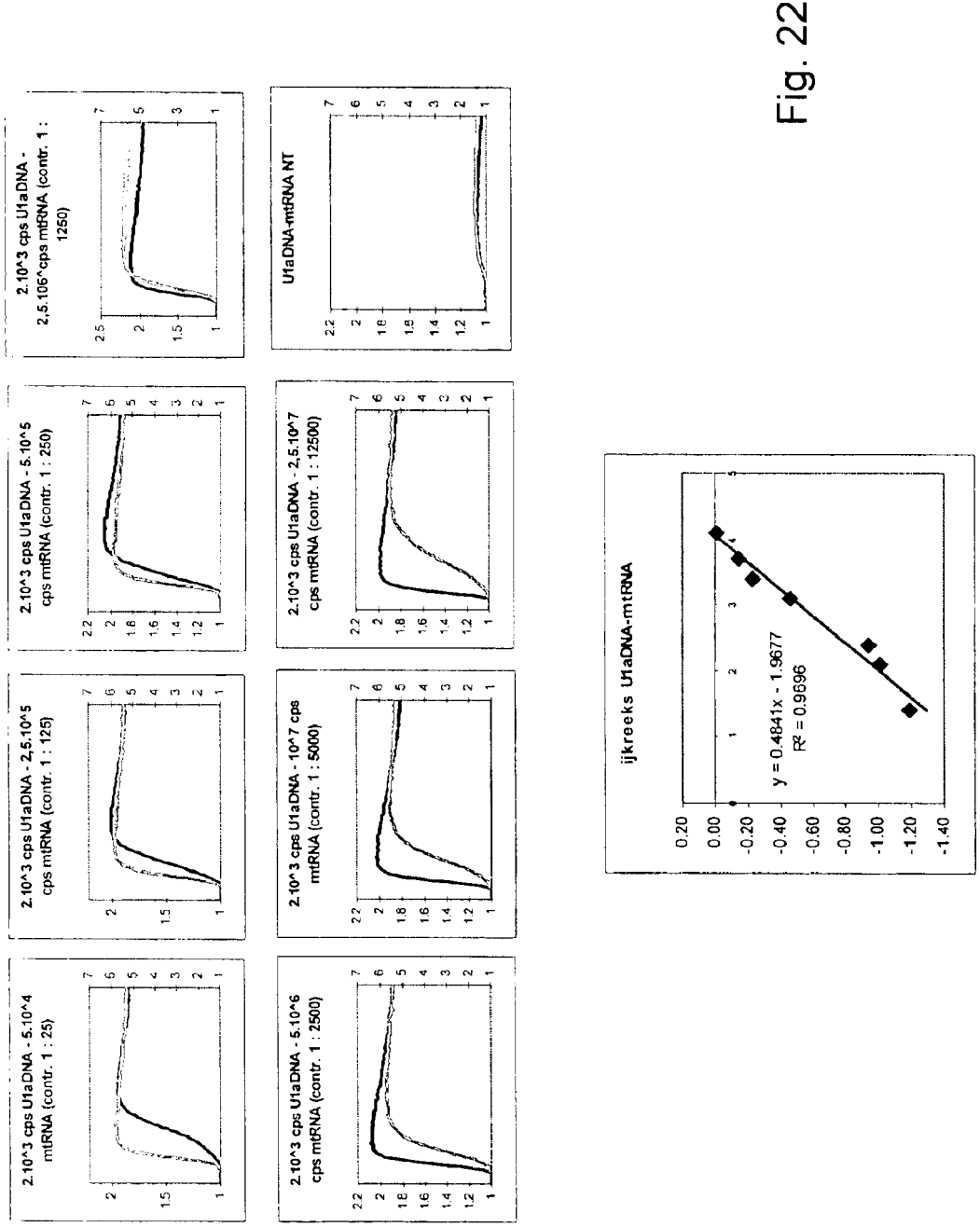
FIG. 22. Fluorescence in time of ROX (chromosomal DNA, grey lines) and FAM (mitochondrial RNA, black lines) fluorescent signal using different ratios of mitochondrial RNA to chromosomal DNA as input. In the lower panel, the linear elation between the ratio of signal and the ratio of RNA and DNA's is shown.
Figure 23:
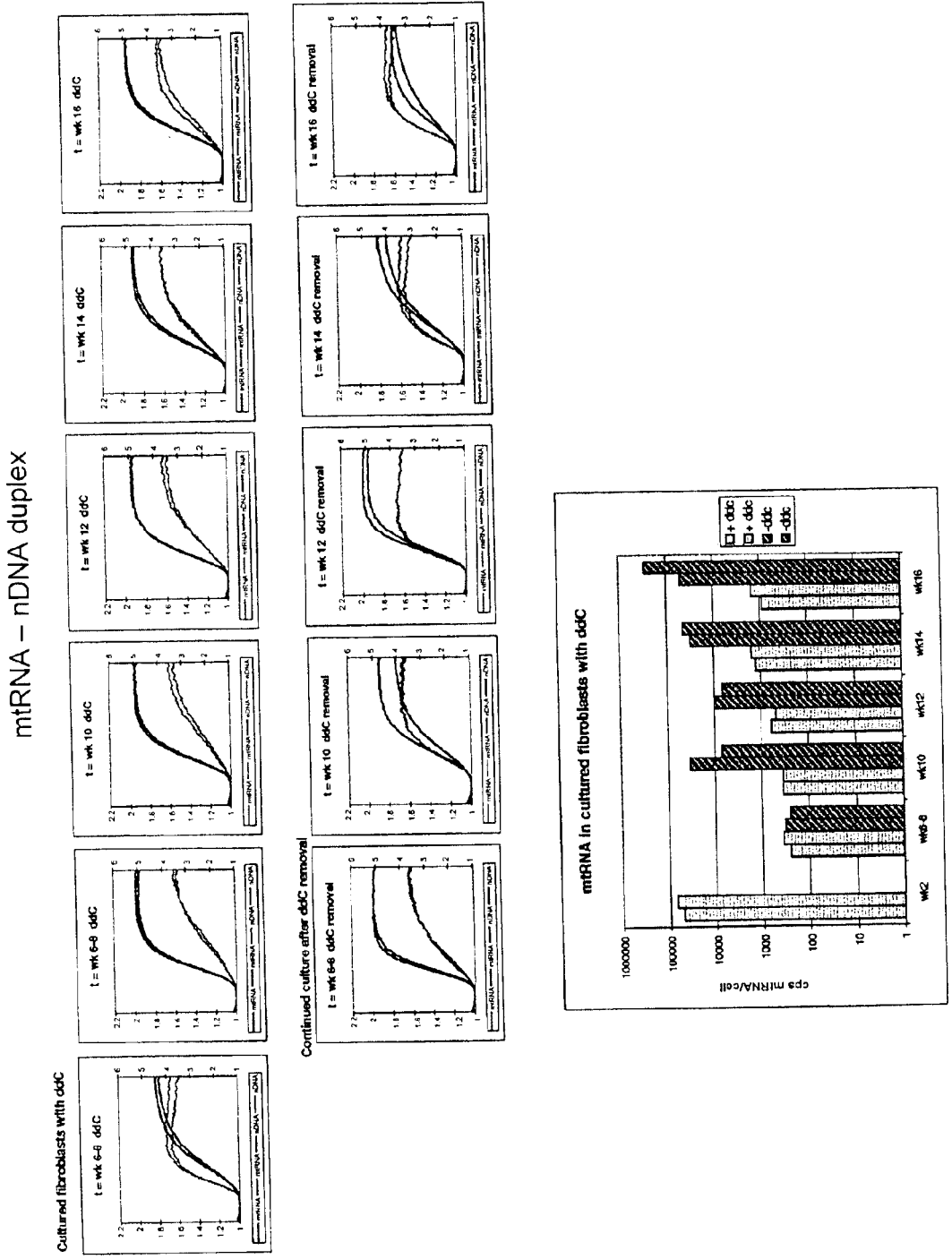
FIG. 23. Bars represent the amount of mitochondrial RNA in fibroblasts cultured in the presence of ddC for the first 8 weeks, after which the culture was continued both with and without ddC until week 16.
Figure 24:
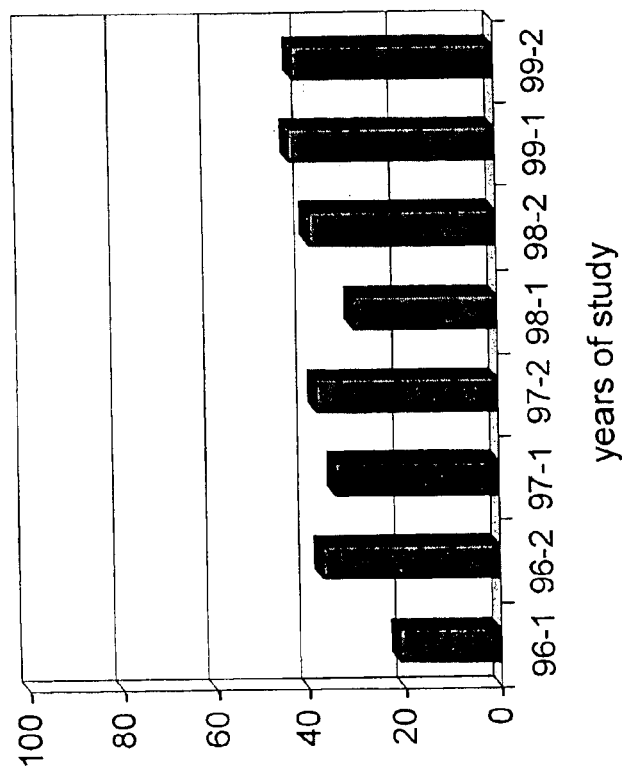
FIG. 24. ATHENA-study of patients changing anti-retroviral treatment because of adverse side-effects.
Figure 25:
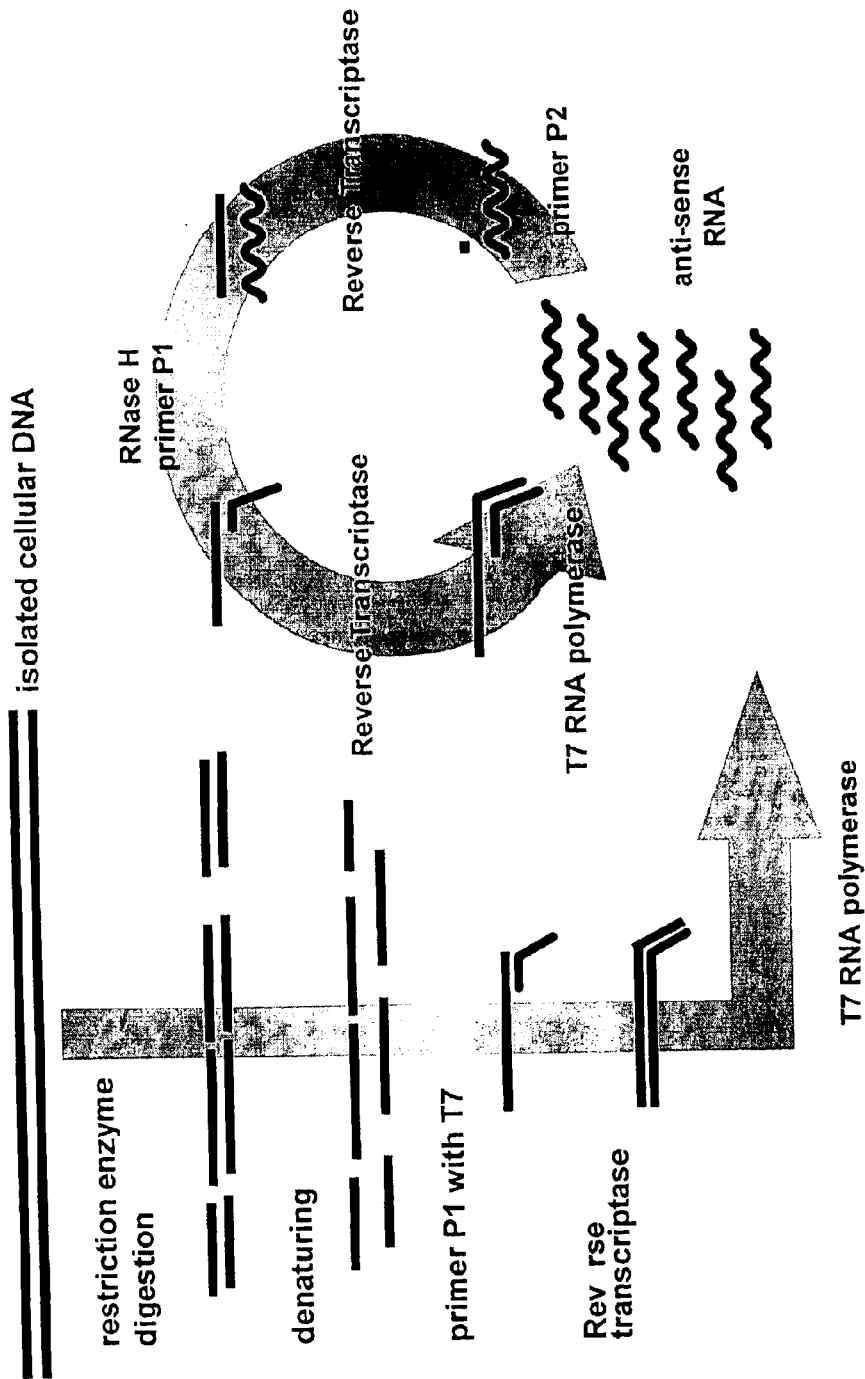
FIG. 25. Schematic representation of DNA-NASBA amplification.
Figure 26:
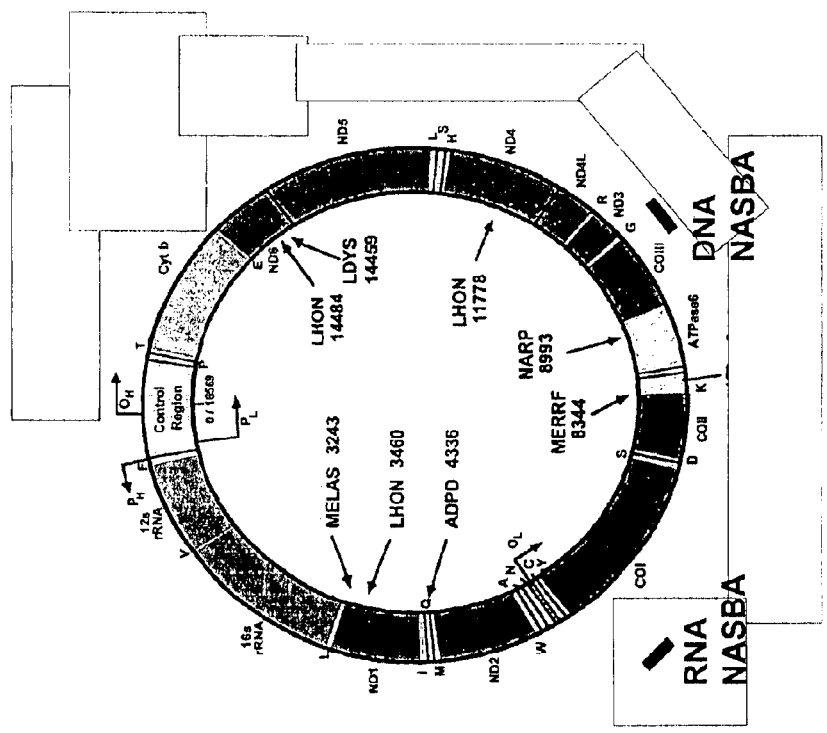
FIG. 26. Genetic map of the mitochondrial DNA with two regions indicated where part of the amplification primers as shown in table 1 are located. Other amplification primers shown in table 1 are located in other regions of the mitochondrial genome and are not indicated in this figure.

References:

1. Saiki, R.K.; Gelfand, D.H.; Stoffel, S.; Scharf, S.J.; Higuchi, R; Horn, G.T.; Mullis, K.B.; Erlich, H.A.: Primer-directed enzymatic amplification of DNA with a thermostable DNA polymerase. Science 239: 487–491, 1988

2. Van Gemen, B.; van Beuningen, R.; Nabbe, A.; Van Strijp, D.; Jurriaans, S.; Lens, P.; Kievits, T.: A one-tube quantitative HIV-1 RNA NASBA nucleic acid amplification assay using electrochemiluminescent (ECL) labelled probes. J.Virol.Methods 49: 157–167, 1994

3. Heid, C.A.; Stevens, J.; Livak, K.J.; Williams, P.M.: Real time quantitative PCR. Genome Res. 6: 986–994, 1996

4. Tyagi, S.; Kramer, F.R.: Molecular beacons: probes that fluoresce upon hybridization. Nat. Biotechnol. 14: 303–308, 1996

5. Leone, G.; van Schijndel, H.; Van Gemen, B.; Kramen, F.R.; Schoen, C.D.: Molecular beacon probes combined with amplification by NASBA enable homogeneous, real-time detection ofRNA. Nucleic Acids Res. 26: 2150–2155, 1998

6. Piatak, M.; Luk, K.C.; Williams, B.; Lifson, J.D.: Quantitative competitive polymerase chain reaction for accurate quantitation of HIV DNA and RNA species. Biotechniques 14: 70–81, 1993

7. De Baar, M.P.; van Dooren, M.W.; de Rooij, E.; Bakker, M.; Van Gemen, B.; Goudsmit, J.; and de Ronde, A.: Single rapid real-time monitored isothermal RNA amplification assay for quantification of HIV-1 isolates from group M, N, and O.J. Clin. Microbiol. 39(4): 1378–1384, 2001

8. Boom, R.; Sol, C.J.; Salimans, M.M.; Jansen, C.L.; Wertheim-van Dillen, P.M.; van der, N.J.: Rapid and simple method for purification of nucleic acids. J.Clin.Microbiol. 28: 495–503, 1990

What is claimed is:

1. A method of determining whether a medicament has therapeutic activity and/or possible side-effects, said method comprising:
   introducing a medicament to an organism;
   determining in a sample obtained from said organism a relative ratio of a mitochondrial nucleic acid and/or gene product thereof to a chromosomal nucleic acid and/or gene product thereof; and
   determining whether there is a change in the relative ratio during and/or after introduction of the medicament, wherein said change in said relative ratio is indicative that said medicament has therapeutic activity and/or possible side-effects.

2. The method according to claim 1, wherein said introducing said medicament comprises introducing said medicament to said organism for at least three months.

3. The method according to claim 1, wherein said medicament is used for treatment of a chronic disease.

4. The method according to claim 1, wherein said introducing said medicament comprises introducing said medicament to an organism free from side-effects at a first time said medicament is introduced to said organism.

5. The method according to claim 1, wherein said therapeutic activity comprises a therapeutic activity against an HIV-related disease and/or a tumor-related disease.

6. The method according to claim 1, wherein said medicament comprises a nucleoside and/or nucleotide analogue.

7. The method according to claim 6, wherein said nucleoside and/or nucleotide analogue is selected from the group consisting of fludarabine, mercaptopurine, tioguanine, cytarabine, flurouracil, gemcyatbine, and mixtures thereof.

8. The method according to claim 1, wherein said medicament comprises AZT, ddI, ddC, d4T, 3TC or tenofofir.

9. The method according to claim 1, wherein said determining said ralative ratio comprises determining said relative ratio prior to said introducing said medicament.

10. The method according to claim 1, wherein said relative ratio of said mitochondrial nucleic acid and/or gene product thereof to said chromosomal nucleic acid and/or gene product thereof is determined in a single assay.

11. The method according to claim 10, further comprising amplifying said mitochondrial nucleic acid and/or gene product thereof and said chromosomal nucleic acid and/or gene product thereof in a single assay.

12. The method according to claim 10, wherein said relative ratio is determined directly by dividing an amount of said mitochondrial nucleic acid and/or gene product by an amount of said chromosomal nucleic acid and/or gene product.

13. The method according to claim 10, wherein said relative ratio is determined directly by dividing an amount of said chromosomal nucleic acid and/or gene product by an amount of said mitochondrial nucleic acid and/or gene product.

14. The method according to claim 10, wherein said relative ratio is determine by comparing said relative ratio to a reference curve.

15. The method according to claim 10, wherein said mitochondrial nucleic acid and/or gene product thereof and said chromosomal nucleic acid and/or gene product thereof are obtained from a peripheral blood mononuclear cell or fibroblast of said organism.

* * * * *

UNITED STATES PATENT AND TRADEMARK OFFICE
CERTIFICATE OF CORRECTION

PATENT NO. : 6,967,016 B2  Page 1 of 1
APPLICATION NO. : 10/006009
DATED : November 22, 2005
INVENTOR(S) : Bob van Gemen et al.

It is certified that error appears in the above-identified patent and that said Letters Patent is hereby corrected as shown below:

On the title page:
In ITEM (56) References Cited   change "of1000 genes." to --of 1000 genes.--

| | |
|---|---|
| COLUMN 12, LINE 11, | change "ethidiumn bromide" to --ethidium bromide-- |
| COLUMN 12, LINE 62, | change "wee" to --were-- |
| COLUMN 15, LINE 57, | change "in one tube The" to --in one tube. The-- |
| COLUMN 16, LINE 46, | change "590/20and" to --590/20 and-- |
| COLUMN 17, LINE 17, | change "4weeks." to --4 weeks.-- |
| COLUMN 18, LINE 30, | change "ddC(30 $\mu$m)" to --ddC (30 $\mu$m)" |
| COLUMN 18, LINE 45, | change "(patient 1 and 2)treated" to --(patient 1 and 2) treated-- |
| COLUMN 22, LINE 50, | change "Bars labeled With" to --Bars labeled with-- |
| COLUMN 24, LINE 27, | change "ofRNA" to --of RNA-- |

In the claims:
CLAIM 9,   COLUMN 38, LINE 66, change "ralative ratio" to --relative ratio--

Signed and Sealed this

Sixteenth Day of December, 2008

JON W. DUDAS
*Director of the United States Patent and Trademark Office*